US012664657B2

(12) United States Patent
Roberts et al.

(10) Patent No.: US 12,664,657 B2
(45) Date of Patent: Jun. 23, 2026

(54) ASSESSMENT OF LUNG DISEASE PROGRESSION

(71) Applicant: QUREIGHT LIMITED, Cambridge (GB)

(72) Inventors: Michael Thomas Roberts, Cambridge (GB); Alessandro Ruggiero, Cambridge (GB); Muhunthan Thillai, Cambridge (GB); Darren John Gallagher, Cambridge (GB)

(73) Assignee: Qureight Limited, Cambridge (GB)

( * ) Notice: Subject to any disclaimer, the term of this patent is extended or adjusted under 35 U.S.C. 154(b) by 75 days.

(21) Appl. No.: 18/274,331

(22) PCT Filed: Jul. 5, 2022

(86) PCT No.: PCT/GB2022/051723
§ 371 (c)(1),
(2) Date: Jul. 26, 2023

(87) PCT Pub. No.: WO2023/281252
PCT Pub. Date: Jan. 12, 2023

(65) Prior Publication Data
US 2024/0127448 A1     Apr. 18, 2024

(30) Foreign Application Priority Data

Jul. 5, 2021     (GB) ...................................... 2109706

(51) Int. Cl.
| | |
|---|---|
| *G06K 9/00* | (2022.01) |
| *G06T 7/00* | (2017.01) |

(Continued)

(52) U.S. Cl.
CPC .............. *G06T 7/0016* (2013.01); *G06T 7/11* (2017.01); *G16H 10/20* (2018.01); *G16H 20/10* (2018.01);
(Continued)

(58) Field of Classification Search
CPC ..................... G06T 7/0016; G06T 7/11; G06T 2207/10081; G06T 2207/10116;
(Continued)

(56) References Cited

U.S. PATENT DOCUMENTS

| | | | |
|---|---|---|---|
| 11,361,440 B2 * | 6/2022 | Wang ..................... | G16H 10/60 |
| 2014/0184608 A1 * | 7/2014 | Robb ..................... | A61B 6/037 345/440 |

(Continued)

OTHER PUBLICATIONS

Shan, Fei, et al. "Lung infection quantification of COVID-19 in CT images with deep learning." arXiv preprint arXiv:2003.04655 (2020) (Year: 2020).*

(Continued)

*Primary Examiner* — Atiba O Fitzpatrick
(74) *Attorney, Agent, or Firm* — Kevin J Fournier IP Legal Services Ltd; Kevin J Fournier

(57) ABSTRACT

A machine learning approach is herein provided for preparing a model for assessing the progression of a lung disease, comprises receiving a first set of segmented images of lungs from different patients with the lung disease. The first set of images is segmented and used to train the model. The trained model is applied to a set of unsegmented images to generate a second set of segmented images. The model is updated with the second set of segmented segmentation. From the model, at least one result associated with progression of the lung disease is outputted.

43 Claims, 9 Drawing Sheets

(51) Int. Cl.

| | |
|---|---|
| *G06T 7/11* | (2017.01) |
| *G16H 10/20* | (2018.01) |
| *G16H 20/10* | (2018.01) |
| *G16H 30/40* | (2018.01) |
| *G16H 50/30* | (2018.01) |
| *G16H 50/50* | (2018.01) |

(52) U.S. Cl.
CPC ............. *G16H 30/40* (2018.01); *G16H 50/30* (2018.01); *G16H 50/50* (2018.01); *G06T 2207/10081* (2013.01); *G06T 2207/10116* (2013.01); *G06T 2207/20084* (2013.01); *G06T 2207/20104* (2013.01); *G06T 2207/30061* (2013.01)

(58) Field of Classification Search
CPC ........... G06T 2207/20084; G06T 2207/20104; G06T 2207/30061; G06T 7/0012; G06T 2207/20081; G06T 9/002; G06T 5/60; G16H 10/20; G16H 20/10; G16H 30/40; G16H 50/30; G16H 50/50; G06V 10/70; G06V 10/82; G06V 10/774–7796; G06V 10/454; G06N 3/08–0985; G06N 3/02–126; G06N 20/00–20; G06F 18/214–2155; G06F 7/023; G06F 40/16; G06K 9/6256; G06K 9/6257; G06K 9/6259; G01N 29/4481
See application file for complete search history.

(56) References Cited

U.S. PATENT DOCUMENTS

| | | | | |
|---|---|---|---|---|
| 2016/0110632 | A1* | 4/2016 | Kiraly ...................... | G06T 7/11 |
| | | | | 382/128 |
| 2020/0285906 | A1* | 9/2020 | Do ......................... | G16H 15/00 |
| 2021/0304408 | A1* | 9/2021 | Chaganti .................. | G06T 7/11 |
| 2021/0304896 | A1* | 9/2021 | Chen ...................... | G16H 50/20 |
| 2021/0398654 | A1* | 12/2021 | Chaganti ............... | G16H 50/80 |
| 2023/0237759 | A1* | 7/2023 | Buckler ................... | G06T 5/73 |
| | | | | 382/128 |
| 2024/0346655 | A1* | 10/2024 | Vlasimsky ............... | G06T 3/40 |

OTHER PUBLICATIONS

Xie, Weiyi, et al. "Contextual two-stage u-nets for robust pulmonary lobe segmentation in ct scans of covid-19 and copd patients." arXiv preprint arXiv:2004.07443 (2020) (Year: 2020).*

\* cited by examiner

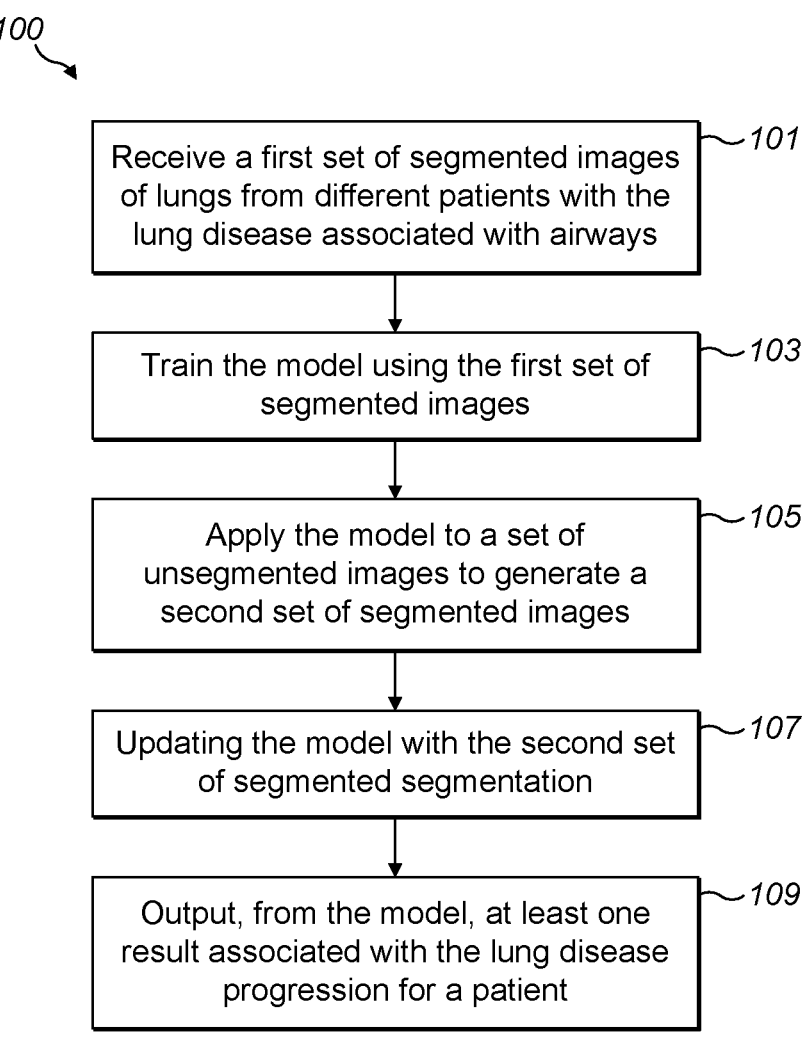

*100*

Receive a first set of segmented images of lungs from different patients with the lung disease associated with airways ~*101*

Train the model using the first set of segmented images ~*103*

Apply the model to a set of unsegmented images to generate a second set of segmented images ~*105*

Updating the model with the second set of segmented segmentation ~*107*

Output, from the model, at least one result associated with the lung disease progression for a patient ~*109*

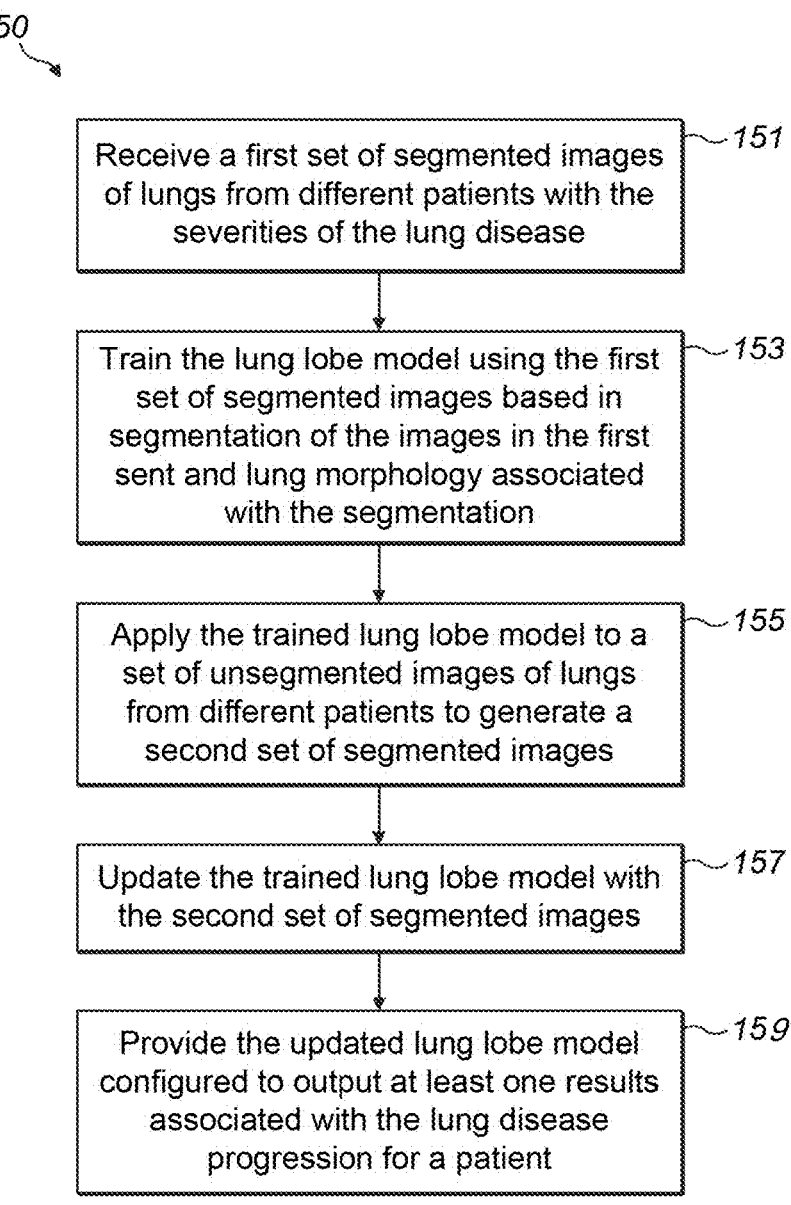

Receive a first set of segmented images of lungs from different patients with the severities of the lung disease — 151

Train the lung lobe model using the first set of segmented images based in segmentation of the images in the first sent and lung morphology associated with the segmentation — 153

Apply the trained lung lobe model to a set of unsegmented images of lungs from different patients to generate a second set of segmented images — 155

Update the trained lung lobe model with the second set of segmented images — 157

Provide the updated lung lobe model configured to output at least one results associated with the lung disease progression for a patient — 159

*FIG. 1B*

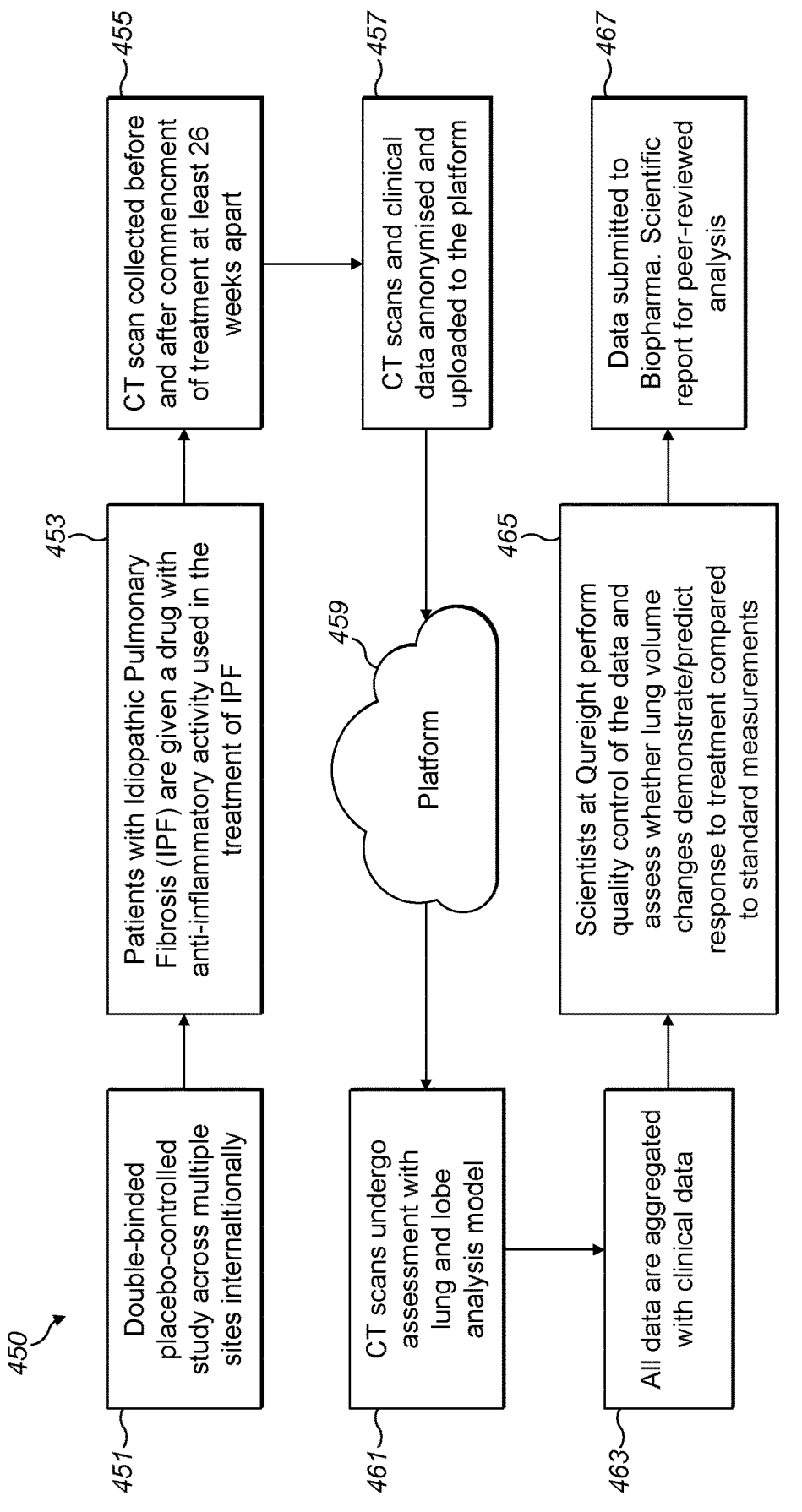

455

CT scan collected before and after commencment of treatment at least 26 weeks apart

457

CT scans and clinical data annonymised and uploaded to the platform

467

Data submitted to Biopharma. Scientific report for peer-reviewed analysis

453

Patients with Idiopathic Pulmonary Fibrosis (IPF) are given a drug with anti-inflammatory activity used in the treatment of IPF

459

Platform

465

Scientists at Qureight perform quality control of the data and assess whether lung volume changes demonstrate/predict response to treatment compared to standard measurements

450

451

Double-binded placebo-controlled study across multiple sites internaltionally

461

CT scans undergo assessment with lung and lobe analysis model

463

All data are aggregated with clinical data

ASSESSMENT OF LUNG DISEASE PROGRESSION

CROSS-REFERENCE TO RELATED APPLICATIONS

This is a national stage application filed under 37 U.S.C. 371 based on International Patent Application No. PCT/GB2022/051723, filed on Jul. 5, 2022, which is based on and claims priority to a United Kingdom Patent Application No. 2109706.8 filed on Jul. 5, 2021, disclosures of which are expressly incorporated by reference herein in their entirety.

TECHNICAL FIELD

The present application relates to a system, apparatus, and method for training and applying an airway model and/or a lung volume model on computed tomography scans to determine lung disease progression for use in clinical applications.

BACKGROUND

Lung diseases are some of the most common medical conditions affecting millions of people around the world. Typical lung disease may be caused by internal and external factors such as smoking, infections, drug-inducted side effects, and gene mutations.

Interstitial lung disease (ILD) is a category of lung disease that affects the interstitium, a thin, delicate lining between alveoli of the lung, whereby tiny blood vessels traverse and permit gas transfer between the alveoli and blood.

One type of ILD is Idiopathic Pulmonary Fibrosis (IPF), with its cause unknown. The NIH's National Library Medicine, states there are ~100,000 IPF patients, (~30,000-40,000 new cases/year). The global IPF treatment market (2020) was $2.2 bn (CAGR|12%, 2022-2027); 2026 expected value $4.3 bn), predominantly in American and European regions (Expert Market Research, Global IPF Treatment Market Outlook). Market drivers include increasing incidence of complex respiratory diseases, ageing, and awareness. In 2018, 79 drug and computational technology products were being developed for IPF. On Feb. 3, 2021, 2,613 industrially funded clinical trials were in setup, recruitment or active trial status for Complex respiratory diseases and 109 studies for IPF.

Patients with IPF show progressive scarring of tissue that could lead to respiratory failure and even death if untreated. There has been no proven treatment for IPF (or other fibrotic lung diseases) until 2014, with the advent of two landmark drugs, Roche's Pirfenidone and Nintedanib from Boehringer Ingelheim. Pirfenidone has shown to reduce the decline in lung capacity/function caused by IPF. In addition to showing similar efficacy as Pirfenidone, Nintedanib demonstrates effectiveness towards non-IPF forms of ILD. Since 2014, over 50 drug candidates have undergone (or presently undergoing) clinical trials for IPF worldwide.

Measuring Forced Vital Capacity (FVC) via a breathing test is a standard approach for diagnosing IPF in hospitals. FVC is a measure of full lung capacity and thus correlates with lung decline. As the fibrosis worsens in the lung, the lung begins to shrink, and FVC decreases. A reduction in the rate of decline of FVC is indicative of a certain level of efficacy from a candidate drug. In clinical trials, FVC is normally used as a primary end-point.

To obtain an accurate measure of FVC is difficult, however. It is equally difficult to assess the progression of the disease solely based on measuring FVC. Thus, there are concerns with FVC as a clinical end-point. These concerns include 1) the breath test is variable depending on the technician who performs it, 2) the test varies within the patient depending on how well or unwell the patient is on the day, and 3) it may not be a true and accurate representation of fibrosis with respect to computed tomography (CT) scans.

Earlier detection of drug potential and patient diagnoses will enhance patient disease stratification. The FDA and EMA are politically supportive of accelerating drug delivery to patients by accelerating technology adoption.

Thus, there is a need for an improved assessment of whether the patient has a type of lung disease affecting the lung's airways. Equally, there is an unmet need for a more efficient way to quantitatively assess lung disease progression in response to the dosage of a new drug candidate in the context of clinical trials.

It is understood that the embodiments described below are not limited to implementations, which solve any, or all of the disadvantages of the exemplary known approaches described above.

SUMMARY

This Summary is provided to introduce a selection of concepts in a simplified form that are further described below in the Detailed Description. This Summary is not intended to identify key features or essential features of the claimed subject matter, nor is it intended to be used to determine the scope of the claimed subject matter; variants and alternative features which facilitate the working of the invention and/or serve to achieve a substantially similar technical effect should be considered as falling into the scope of the invention disclosed herein.

The present disclosure provides a machine learning approach to assess the progression of lung disease affecting airways using segmented lung images or computed tomography (CT) scans and iterative training the machine learning model (airway model) assisted by feedback from human experts. The airway model is prepared by receiving a first set of segmented images of lungs from different patients with the lung disease associated with airways. The airway model is trained using the first set of segmented images. The airway model is applied to a set of unsegmented images to generate a second set of segmented images. The airway model is updated with the second set of segmented segmentation. From the model, at least one result associated with the lung disease progression is outputted for use with various clinical applications.

The present disclosure further provides a lung volume model or lung lobe model applicable to various clinical applications. The lung lobe model is also trained in a similar manner, except for the difference in how the CT images or training data is annotated; for example, the training data may delineate each lobe of the lung and their corresponding 3-dimensional volume as opposed to the airway patterns.

The preparation of the lung lobe model comprises two stages. In the first stage, a lung segmentation algorithm is used, specifically trained to segment lungs with different seventies of IPF. In the second stage, the model uses the image of the segmented lung and segments this into the 5 different lobes of the left and right lungs. Both stages rely on multiple CNNs arranged in a pipeline, with each part of the pipeline considering the image at different resolutions. Similar to the airway model, the lung lobe model or the underlying neural network outputs lung disease progression results in accordance with the lung volume of the patient.

In a first aspect, the present disclosure provides a computer-implemented method of preparing a lung lobe model for assessing progression of a lung disease, the method comprising: receiving a first set of segmented images of lungs from patients with different severities of the lung disease, wherein the images in the first set are segmented using a trained lung segmentation model; training the lung lobe model using the first set of segmented images based on segmentation of the images in the first set and lung morphology associated with the segmentation, wherein the lung morphology comprises at least lobes of left and right lungs; applying the trained lung lobe model to a set of unsegmented images of lungs from different patients to generate a second set of segmented images, wherein the set of unsegmented images corresponds to the first set of segmented images; updating the trained lung lobe model with the second set of segmented images; and providing the updated lung lobe model configured to output at least one results associated with the lung disease progression of a patient.

In a second aspect, the present disclosure provides a computer-implemented method of preparing an airway model for assessing progression of a lung disease, the method comprising: receiving a first set of segmented images of lungs from different patients with the lung disease associated with airways, wherein the first set of images is segmented manually based on a generational level of airway; training the model using the first set of segmented images, wherein the model is configured to segment the airways based on airway morphological parameters; applying the model to a set of unsegmented images to generate a second set of segmented images, wherein the set of unsegmented images corresponds to the first set of segmented images; updating the model with the second set of segmented segmentation; and outputting, from the model, at least one result associated with the lung disease progression for a patient.

In a third aspect, the present disclosure provides a method for conducting pharmaceutical drug testing to ascertain a response of a candidate drug comprising: administering the candidate drug to a patient affected by lung disease; and measuring a reaction of the patient to the administration of the candidate drug utilizing a trained airway model and/or a trained lung lobe model, wherein each model is configured to: receive a first set of unsegmented images from the patient before administration of the candidate drug and a second set of unsegmented images after the administration of the candidate drug; determine a baseline of disease progression according to a first set of unsegmented images; determine the response of disease progression according to a second set of unsegmented images; and measure the reaction from the patient based on the baseline and the response.

In a fourth aspect, the present disclosure provides a method for conducting pharmaceutical drug screening to ascertain a response of a candidate drug for lung disease, the method comprising: measuring a reaction of a patient suffering from lung disease to whom the candidate drug has been administered utilizing a trained airway model and/or a trained lung lobe model, wherein the trained airway model and/or the trained lung lobe model is configured to: receive a first set of unsegmented images from the patient before administration of the candidate drug and a second set of unsegmented images after the administration of the candidate drug; determine a baseline of disease progression according to a first set of unsegmented images; determine the response of disease progression according to a second set of unsegmented images; and measure the reaction from the patient based on the baseline and the response.

In a fifth aspect, the present disclosure provides a system for supporting a clinical study, the system comprising: one or more data storages and at least one processor configured to: receive computed tomography (CT) scans of a patient with lung disease, wherein the CT scans are collected from at least two time points, at least one time point collected before the patient has been administered a drug, and one or more time points after the patient has been administered the drug; generate a data set associated with progression of the lung disease from the CT scans applying a trained airway model and/or a trained lung lobe model; analyse the data set in response to the time point of drug administration; determine a drug-induced effect based on the analysis; and transmit the determination in support of the clinical study.

In a sixth aspect, the present disclosure provides an apparatus comprising a processor comprising a processor, a memory and a communication interface, the processor connected to the memory and communication interface, wherein apparatus is adapted or configured to: prepare an airway model for assessing progression of a lung disease, the method comprising: receiving a first set of segmented images of lungs from different patients with the lung disease associated with airways, wherein the first set of images is segmented manually based on a generational level of airway; training the model using the first set of segmented images, wherein the model is configured to segment the airways based on airway morphological parameters; applying the model to a set of unsegmented images to generate a second set of segmented images, wherein the set of unsegmented images corresponds to the first set of segmented images; updating the model with the second set of segmented segmentation; and outputting, from the model, at least one result associated with the lung disease progression for a patient.

In a seventh aspect, the present disclosure provides an apparatus comprising a processor comprising a processor, a memory and a communication interface, the processor connected to the memory and communication interface, wherein apparatus is adapted or configured to: conduct pharmaceutical drug testing or screening to ascertain a response of a candidate drug for lung disease, the method comprising: measuring a reaction of a patient suffering from lung disease to whom the candidate drug has been administered utilizing a trained airway model and/or a trained lung lobe model, wherein each model is configured to: receive a first set of unsegmented images from the patient before administration of the candidate drug and a second set of unsegmented images after the administration of the candidate drug; determine a baseline of disease progression according to a first set of unsegmented images; determine the response of disease progression according to a second set of unsegmented images; and measure the reaction from the patient based on the baseline and the response.

In an eighth aspect, the present disclosure provides a system for supporting a clinical study, the system comprising: one or more data storages and at least one processor configured to: receive computed tomography (CT) scans of a patient with lung disease, wherein the CT scans are collected from at least two time points, at least one time point collected before the patient has been administered a drug, and one or more time points after the patient has been administered the drug; generate a data set associated with progression of the lung disease from the CT scans applying a trained airway model and/or a lung lobe model; analyse the data set in response to the time point of drug administration; determine a drug-induced effect based on the analysis; and transmit the determination in support of the clinical study.

The methods described herein may be performed by software in machine-readable form on a tangible storage medium e.g. in the form of a computer program comprising computer program code means adapted to perform all the steps of any of the methods described herein when the program is run on a computer and where the computer program may be embodied on a computer-readable medium. Examples of tangible (or non-transitory) storage media include disks, thumb drives, memory cards etc. and do not include propagated signals. The software can be suitable for execution on a parallel processor or a serial processor such that the method steps may be carried out in any suitable order, or simultaneously.

This application acknowledges that firmware and software can be valuable, separately tradable commodities. It is intended to encompass software, which runs on or controls "dumb" or standard hardware, to carry out the desired functions. It is also intended to encompass software, which "describes" or defines the configuration of hardware, such as HDL (hardware description language) software, as is used for designing silicon chips, or for configuring universal programmable chips, to carry out desired functions.

The preferred features described in the following section may be combined as appropriate, as would be apparent to a skilled person, and may be combined with any of the aspects of the invention.

BRIEF DESCRIPTION OF THE DRAWINGS

Embodiments of the invention will be described, by way of example, with reference to the following drawings, in which:

FIG. 1A is a flow diagram illustrating an example of preparing an airway model for the assessment of lung disease progression according to the invention;

FIG. 1B is a flow diagram illustrating an example of preparing a lung lobe model for the assessment of lung disease progression according to the invention;

FIG. 4B is a system diagram illustrating an example of an lung lobe model used in the con-text of the drug discovery according to the invention;

Figure 2:
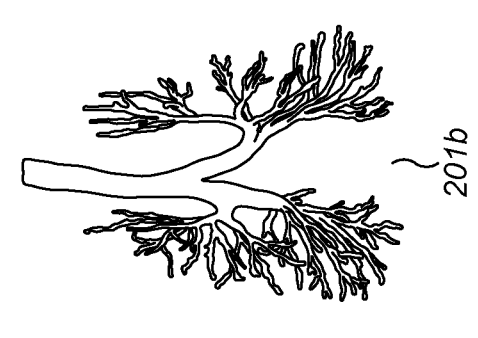
FIG. 2 is a pictorial diagram illustrating an example of unsegmented and segmented images of lungs according to the invention.

Common reference numerals are used throughout the figures to indicate similar features.

DETAILED DESCRIPTION

Embodiments of the present invention are described below by way of example only. These examples represent the suitable modes of putting the invention into practise that are currently known to the applicant, although they are not the only ways in which this could be achieved. The description sets forth the functions of the example and the sequence of steps for constructing and operating the example. However, the same or equivalent functions and sequences may be accomplished by different examples.

Lung disease progression in patients is typically assessed visually by expert radiologists. For each patient, the experts may study up to 300 images of their computed tomography (CT) scan before making visual assessments based on the appearance and size of the patient airways or size of the patient's lungs and shape while noting any observable changes over time. The fibrosis progression induces an architectural distortion of the lung tissue with volume loss. Visual assessment can only yield qualitative data. There can be considerable variation between radiologists in their interpretation of the same dataset. Thus, with limited expert resources, accurate assessment/analysis takes a long time.

Further, analysis of images from a CT scan has also been shown to be subjective. There can be considerable variation between radiologists in terms of their interpretation of the same image. This variation reduces with increased radiologist experience—variation in image interpretation reduces within a pool of consultant radiologists compared to a pool of more junior radiologists.

Analysis by eye can only yield qualitative data. Quantitative assessments with any level of precision in airway volume may not be possible when calculating back from images by hand or eye. Quantitative analysis is highly desirable for airway volume measurements to become integrated into assessments regarding patient disease progression and drug response. Recent research indeed pointed towards lung airway volume change as a potentially sensitive biomarker for disease progression in interstitial lung disease.

Recent research also pointed toward lung volumes as a potentially sensitive biomarker for disease progression in interstitial lung disease. Similar, assessment/analysis of lung volumes is impossible however without a tool that quantitatively segments the lungs and extracts volumes. Manual segmentation of the lung structure is possible but is very time-consuming and not performed in clinical practice. Quantitative analysis is highly desirable for lung volume measurements to become integrated into patient disease progression and drug response assessments.

There may be commercial (non-specialised) algorithms available, the workings of which are however unpredictable and not validated, as are the datasets used to train the algorithms and whether those training sets could come from healthy or diseased lungs. Existing commercial algorithms have been developed without any specific disease use in mind, but for generic utility across healthy and diseased lungs across all lung conditions. Some of these developed tools allow the segmentation of the whole lung but not the separation in different lobes. Since IPF involves predominantly lower lobes, a tool that can focus quantitative measurements on these critical areas is needed.

It is understood that different diseases may have disparate effects on the lung airways. These diseases may come with other attributes that make imaging of the lung complicated in terms of segmentation (e.g. fibrosis and inflammation). The result is that in the case of images for patients with interstitial lung diseases, non-specialised algorithms (i.e. the available commercial algorithms) may not be applicable for accurate airway detection and lung volume measurement and therefore, the signs that may indicate the early onset of severe disease go undetected.

Accordingly, these non-specialised algorithms would not be suitable for use with images from patients with interstitial lung disease to generate accurate data to inform clinicians about disease progression and drug response.

Finally, there are certain open-source algorithms, the workings and training of which are similar to existing commercial algorithms. The level of validation/effort gone into their development varies. They lack consistency when used to assess a specific disease. Such is the complexity of interstitial lung disease in its effects on surrounding lung tissue and airways, segmentation and measurement of airways for images from patients with interstitial lung diseases, open-source approaches lack the critical mass of training set data and expert input to achieve accurate, reliable performance and indeed makes such open-source algorithms unsuitable for use with images from patients with interstitial lung diseases.

The present invention described herein overcomes at least some of the above shortcomings in the existing approaches/algorithms by providing an improved airway model and/or an improved lungs and lobes model for assessing the progression of lung disease affecting airways. The present invention also provides an efficient way to quantitatively evaluate lung disease progression in the context of drug discovery, for example, in response to the dosage of a new drug candidate, thus solving any or all of the issues with the exemplary known approaches described above.

Herein describes a fully automated airway model as part of the present invention that assesses lung disease progression affecting airways. The lung disease may be Idiopathic Pulmonary Fibrosis (IPF) or related interstitial lung disease (ILD). For example, the model provides airway measurement and correlates with radiological disease progression in Idiopathic Pulmonary Fibrosis (IPF). In the example, radiologists may be employed to delineate or annotate airways shown on the CT images from patients suffering from IPF or potentially suffering from IPF. The annotated images are used for training the airway model, where the model may be a multistage conventional neural network to enable end-to-end segmentation from a full CT volume. The airway model allows for improving the assessment of whether a patient has IPF or to which stage the IPF has progressed. Moreover, the airway model is applicable to quantify lung disease progression in response to the dosage of a drug candidate in a clinical trial by measuring the reaction before and after the drug has been administered.

In addition to the airway model described herein, the present disclosure also provides a lung volume model (or interchangeably lung lobe model) for assessing the progression of lung disease in a similar manner and for treating like diseases. In general, the lung volume model comprises two stages. In the first stage is a lung segmentation algorithm, specifically trained to segment lungs with different severities of IPF. The second stage uses the image of the segmented lung and segments this into the 5 different lobes of the left and right lungs. Both stages and the underlying algorithms rely on multiple CNNs arranged in a pipeline, with each part of the pipeline considering the image at different resolutions. The difference between the two stages is with respect to image resolution and the application masks, as described in the following sections. More specifically, in the first stage, the lung volume model, the convolutional network may be applied to unsegmented images following initial training. In the second stage, the lobe model, the CNN may be applied to segmented lung images. Manual check and correction (where required) of the errors and or inconsistencies (human-in-the-loop to create a new segmented dataset as "ground truth") to the extent that the model may undergo repeated validation with one or more set of unsegmented CT images of the lungs (not previously seen by the algorithm). The output of the validated model or the model itself may be used for further clinical applications as described throughout this application and illustrated in the following figures.

The respective applications of the airway model and lung volume model are to quantify airway volume and lung and lobes volume more precisely so the resultant quantification may be used as a biomarker for assessing lung disease progression in place of or in addition to standard Forced Vital Capacity (FVC).

Moreover, these models also provide further advantages in relation to administering treatment for patients as well as in clinical trial environments. These advantages include:
- a) It may be a more sensitive marker than FVC for early IPF progression (useful to monitor 'mild' patients who are starting to get worse);
- b) It is a closer representation of the CT radiology change in fibrosis than FVC;
- c) It may supplement FVC as a more sensitive marker of progression according to the data shown in FIG. 5;
- d) It may allow Biopharma/clinical trials to happen faster (e.g. measure a drug across 2 CT scans 12 weeks apart—the previous trials have needed to use 52 weeks of FVC change which is a long and expensive study);
- e) It may allow cohort selection, i.e. identify patients on trials who are progressing their fibrosis so are best suited for a drug intervention; and
- f) It may allow monitoring of the drug over time in both a trial and the real world, i.e. using change in airway volume and/or lungs/lobes volumes to see if a drug is working.

These models are trained iteratively using segmented data. They provide a rapid, consistent, automatic, accurate segmentation and measurement of lung lobes and airways and their volumes for images from interstitial lung disease patients allowing confident assessments to be made regarding patient disease progression and treatment response based on new information demonstrating lung volume and airway volume changes, and serve as a sensitive biomarker in the clinical study and treatment of from interstitial lung diseases.

In the context of the airway model, a training set of CT images is identified. The CT images may be generated using or derived from a device or scanner adapted to produce CT scans. The device or scanner may have an X-ray source accompanied by computational methods for produce a cross-sectional image of an object. The training set suitably captures many nuances of images (cross-section of lung images from different perspectives) from patients suspected of suffering from an interstitial lung disease, representing the challenges that expert radiologists experience in precise and accurate classification and measurement of airway changes. These CT images may be segmented in terms of airways by a team of expert radiologists. The airway model is constructed from the training set. The airway model comprises a convolutional neural network algorithm suitable for image segmentation. The algorithm was modified or updated to cope with the challenges of segmenting and measuring airways from CT images from patients suspected of suffering from interstitial lung disease. The algorithm is thereby trained on the training dataset.

Further algorithm modifications/updates are then made to cope with the challenges of segmenting and measuring central and peripheral airways from CT images from patients suspected of suffering from an interstitial lung disease, given the random airway branching and decreasing diameter of airways of interest. These interested airways may comprise at least the trachea, main bronchi, lobar bronchi, segmental, and subsegmental bronchi. The algorithm may be presented with new CT images, and the algorithm is configured to classify and quantify these new images according to lung texture classification embedded from prior training. The output from the algorithm may be presented to the expert radiology team. Any error in the output image classification may be corrected by the team or via other automated means, and the algorithm may update its parameter for any correction or adjustment. The algorithm may be updated in an iterative manner. The update repeats until the algorithm is fully retrained based on expert intervention and the choice of challenging images.

The manual segmentation is performed with respect to a generational level of the airways, or more specifically, up to a generation of distal airways. At an airway generation or generational level is where one airway branches into two or more narrower airways. The human respiratory tree or airway system may be partitioned into 23 generations or generational levels to which they are used to transport gases from the trachea down to the acini. These 23 generations or generational levels of dichotomous branching extend from the trachea (generation 0) to the last order of terminal bronchioles (generation 23). At each generation, each airway is divided into two smaller daughter airways. The conducting zone is between generations up to 16, including trachea, bronchi, bronchioles, and terminal bronchioles, while acinus is between generations 17 to 23, including respiratory bronchioles, alveolar ducts, and alveolar sacs. The terminal bronchioles, generation 16, are divided into respiratory bronchioles or transitional bronchioles, generations 17-19. These respiratory bronchioles further divide into alveolar ducts, generations 20-22, which are completely lined with alveoli. These generations or generational levels are illustrative of the manual segmentation performed for training the airway model.

The segmentation of an image may be dividing or partitioning the image into various parts called segments. The entire image may be processed simultaneously, as there may be areas of the image that contain little or no information. By dividing the image into segments, important segments may be further processed by the airway model. An example of the segmentation of CT images is shown in FIG. 2. The CT images may be in high-resolution with thinner slicing or slice. The manually segmented lung images may be used to train and retrain the airway model until an accurate representation of the airway is achieved.

In the context of the lungs/lobes model, a training set of CT images is identified. The CT images may be generated using or derived from a device or scanner adapted to produce CT scans. The device or scanner may have an X-ray source accompanied by computational methods to produce a cross-sectional image of an object. The training set suitably captures many nuances of images (cross-section of lung images from different perspectives) from patients suspected of suffering from an interstitial lung disease, representing the challenges that expert radiologists experience in precise and accurate classification and measurement of airway changes.

These lungs and lobes on CT images may be segmented by a team of expert radiologists. The lungs/lobes model is constructed from the training set. The lung/lobes model comprises a convolutional neural network algorithm suitable for image segmentation. The algorithm was modified or updated to cope with the challenges of segmenting and measuring airways from CT images from patients suspected of suffering from interstitial lung disease. The algorithm is thereby trained on the training dataset.

Further algorithm modifications/updates are then made to cope with the challenges of different depths of inspiration during the scan, which may have effects on the reproducibility of the volumetric measurements in a longitudinal assessment of the same patient. Co-registration tools or correction systems can be implemented.

Figure 3:
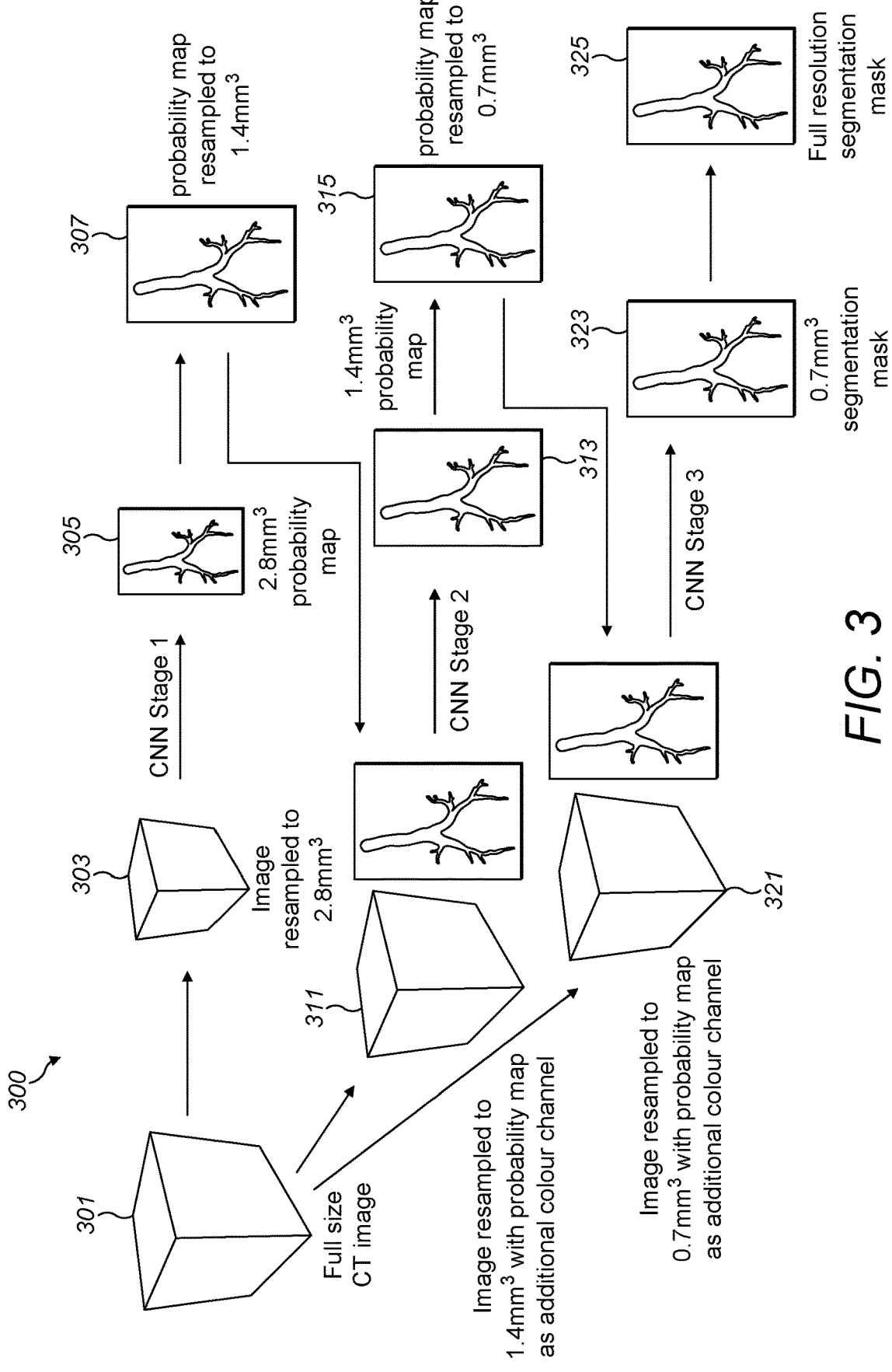
FIG. 3 is a schematic diagram illustrating an example of an airway model according to the invention.

The airway model and/or lungs and lobes model may be a type of convolutional network algorithm. The training of the airway model or the underlying network may be supervised, semi-supervised, or unsupervised, depending on the segmentation and the training criteria. The network may be a 2D or 3D multistage convolutional network. The network may use kernels and/or filters to extract features from the segmented image. The image is sharpened in the process. The various stages of the convolutional network may employ different configurations. These stages correspond to the diameters of the airway or other features. Exemplary stages of the network are shown in FIG. 3 and further described in the corresponding sections. The hyperparameters of the airway models may include but are not limited to learning rate, the batch size or the number of epochs which may be optimized using searches and visualizations. The model parameters are updated in relation to the training data.

The convolutional network may be configured to segment airways based on airway morphological parameters. Since the airways are not a static structure, their morphology is thereby influenced by the properties of the surrounding elastic matrix. The morphological parameters may include but are not limited to the airway size, airway diameter, airway volume, a pattern of airway branching, and degree of airway branching. The airway diameter may be associated with a tissue condition in relation to a stage of disease progression, where the tissue condition comprises healthy tissues and traction bronchiectasis.

The convolutional network may be applied to unsegmented images following the initial training such that the overlay of the manual segmentation and segmentation performed by the algorithm. Manual check and correction (whereas required) of the errors and or inconsistencies (human-in-the-loop to create a new segmented dataset as "ground truth") to the extent that the model may undergo repeated validation with one or more sets of unsegmented CT images of the lungs (not previously seen by the algorithm). The output of the validated model or the model itself may be used for further clinical applications as described throughout this application and illustrated in the following figures.

In the context of using the airway or lung model in relation to clinical application, trial, testing, or screening described herein, it would be understood that the application, trial, testing, or screening are under controlled conditions and with the informed consent of the patient in the event that the trial, testing, or screen will be performed on the patient.

The following table shows an example of the airway and lung models in relation to the machine learning techniques applied. The table details the difference between the model implementation training data being the training data, the segmented airway images vs. segmented lung lobes images, as presented in accordance with FIGS. 1 to 6.

TABLE 1

| | Airway model | Lung model |
|---|---|---|
| Input data formats | 3D images, in common imaging formats, such as Nifti | 3D images, in common imaging formats, such as Nifti |
| Network topology (nodes, number of layers, arrangement of nodes and layers | 3D U-Net Convolutional Neural Network. Channels in each block increasing along [16, 32, 64, 128] with stride 2. | 3D U-Net Convolutional Neural Network. Channels in each block increasing along [16, 32, 64, 128] with stride 2. |
| Models | 3D UNet | 3D UNe |
| Connectivity (feedback, feedforward) | Feed forward | Feed forward |
| Propagation function | ADAM optimiser | ADAM optimiser |
| Weights | Initialised randomly, updated through training | Initialised randomly, updated through training |
| Transfer or activation functions | Parametric ReLU | Parametric ReLU |
| Learning paradigms - supervised, and supervised, reinforcement | Supervised | Supervised |
| How learning data is selected and now training set is composed | Radiologist segmentations of the airways of a representative subset of the overall dataset | Radiologist segmentations of the lung lobes of a representative subset of the overall dataset |
| Cost functions | Dice loss | Dice loss |

FIG. 1A is a flow diagram illustrating an example process 100 for preparing an airway model to assess disease progression in a patient's lung. The first set of segmented images of lungs is used as data for training an airway model, where the model is configured to segment the airways based on airway morphological parameters such as airway size, airway diameter, airway volume, a pattern of branching, and degree of airway branching, and any pattern or the absence thereof. Optionally, the airway diameter may be associated with a tissue condition in relation to a stage of disease progression, where the tissue condition comprises healthy tissues and traction bronchiectasis.

Following the training, the model is applied to a set of unsegmented images to generate a second set of segmented images. The segmented images are used to update the model. This could be done iteratively to the extent of outputting at least one result for understanding disease progression. Such a result is thereby associated with the lung disease progression of the patient. The steps of process 100 are as follows:

In step 101, the airway model receives the first set of segmented images. The images are manually segmented by or based on a generational level of the airway. For example, the manual segmentation or annotation may be done by expert thoracic radiologists. These experts may segment or perform segmentation up to the visible generation of distal airways for images from different patients suffering from or likely suffering from lung disease associated with airways. Such lung disease may be IPF or related ILDs. The related ILDs include but are not limited to interstitial pneumonia, nonspecific interstitial pneumonitis, hypersensitivity pneumonitis, cryptogenic organizing pneumonia, acute interstitial pneumonitis, desquamative interstitial pneumonitis, sarcoidosis, and asbestosis.

In step 103, the model is trained using the first set of segmented images. The model may be a multistage convolutional neural network or a type of convolutional neural network that accommodates processing segmented CT images. The network may also accommodate high-resolution CT images.

The network is configured to encompass multiple stages, with each stage associated with learning an aspect of the patient's airway. The airway model is thereby configured to segment the airways based on airway morphological parameters. The configured model is adapted to capture the spatial and temporal dependencies in an input image.

In step 105, the model is applied to a set of unsegmented images, where the set of unsegmented images corresponds to the first set of segmented images to generate a second set of segmented images. Applying the model to the unsegmented images lets images that are manual segmentation be overplayed with images that are automatically segmentated by the model. Overlaying the images enables checking and correcting errors and/or inconsistencies, providing means of validation via a human-in-the-loop approach. Establishing new segmentation on the dataset also serves as ground truth training labels.

In step 107, the model is updated with the second set of segmented images to establish necessary embedding within the network structure based on the ground truth. The model may be validated. The model may be inputted with a new set of unsegmented images and output the validation results from the model. The model may be refined based on external input from a user, where the external input is associated with one or more corrections to the outputted validation results.

Further, this process may be iterative. The refinement of the model may iterate until the model achieves a predetermined threshold in accurately classifying one or more new sets of unsegmented lung images. The validation results or results of the model may be compared to one or more annotated lung images of a healthy patient and/or a patient suffering from lung disease to assess disease progression associated with each image from the set of unsegmented lung images.

In step 109, the model outputs at least one result associated with the lung disease progression of a patient. The output may be used in the clinical context. One use of the results from the model may be used to determine a dosage regimen for administering antifibrotics drugs to treat lung disease, where lung disease is a type that affects lung airways, including IPF or related ILDs.

Moreover, when determining a dosage regimen, such determination may be achieving a clinical end-point for administering the drug for treating airway lung diseases such as IPF and related ILDs.

FIG. 1B is a flow diagram illustrating an example of preparing a lung lobe or lung volume model 150 to assess disease progression in a patient's lung. First, the segmented images of lungs are received from patients with different severities of lung disease. The lung lobe model is trained using the first set of segmented images based on the segmentation of the images in the first set and lung morphology associated with the segmentation. The trained lung lobe model is applied to a set of unsegmented images of lungs from different patients to generate a second set of segmented images. The trained lung lobe model is updated with the second set of segmented images such that to provide the updated lung lobe model. The updated lung lobe model is configured to output at least one result associated with the lung disease progression of a patient. Said at least one result may be used for monitoring the progression of the lung disease in response to drug treatment.

In step 151, the first set of segmented images of lungs is received from patients with different severities of the lung disease as input to the lung lobe model. The various images in the first set may be segmented using a trained lung segmentation model. The first set of segmented images may comprise segmented lung images masked by segmentation of the lungs derived using the trained lung segmentation model from a set of unsegmented computed tomography (CT) images of lungs.

The lung segmentation model for segmenting the first set of images is configured to: 1. receive a set of unsegmented computed tomography (CT) images of lungs; 2. process unsegmented CT images of lungs at one or more resampling dimensions in relation to a probability map; 3. generate the probability map associated with said one or more resampling dimensions; and 4. provide the first set of segmented images from the unsegmented CT images of lungs based on the probability map. It is understood that the first set of segmented images is provided at a full image resolution corresponding to an original image resolution of the set of unsegmented CT images of lungs.

The lung segmentation model may be trained by first receiving a set of computed tomography (CT) images of lungs annotated with at least one designated segmentation. For example, the designated segmentation of images may be annotated by expert thoracic radiologists who identify the lung lobes and manually delineate their border by using an image annotation tool.

Subsequently, the set of annotated CT images of lungs is processed based on the said at least one designated segmentation at one or more resampling dimensions. The probability map is generated, where the map is associated with said one or more resampling dimensions in relation to said at least one designated segmentation. The trained lung segmentation model is provided for segmentation as part of the first stage. The trained lung segmentation model comprises the generated probability map in accordance with the designated segmentation.

In step 153, the lung lobe model is trained using the first set of segmented images based on the segmentation of the images in the first set and lung morphology associated with the segmentation. The associated lung morphology comprises at least lobes of the left and right lungs. For example, 3 lobes on the right and 2 lobes on the left anatomically. There may be anatomical variations of incomplete separation of the lobes. The lung lobe model may be a multistage convolutional neural network or a type of convolutional neural network that accommodates processing segmented CT images. The network may also accommodate high-resolution CT images.

More specifically, the model is configured to encompass multiple stages, with each stage associated with learning an aspect of the patient's lungs and lobes. The lung lobe model is thereby configured to segment the lungs/lobes based on their morphological parameters. The configured model is adapted to capture the spatial and temporal dependencies in an input image similar to the airway model.

In step 155, the trained lung lobe model is applied to a set of unsegmented images of lungs from different patients to generate a second set of segmented images. The set of unsegmented images may correspond to the first set of segmented images. It is understood that the images with the lungs segmented are used for training data in the lobe segmentation algorithm. As with the airway model, overlaying these images may enable checking and correcting errors and/or inconsistencies, providing means of validation via a human-in-the-loop approach; thus establishing new segmentation on the dataset also serves as ground truth training labels.

In step 157, the model is updated with the second set of segmented images to establish necessary embedding within the network structure based on the ground truth. The model may be validated. In particular, the model may receive a new set of unsegmented images for validation and outputting the validation results from the model. As an option, the validation results may be compared to one or more annotated lung images of a healthy patient and/or a patient suffering from lung disease to assess disease progression associated with each image from the set of unsegmented lung images.

In step 159, the updated lung lobe model as provided is configured to output at least one result associated with the lung disease progression of a patient. Specifically, the trained lung lobe model outputs said at least one result associated with the lung disease progression of the patient based on a new set of unsegmented lung images from the patient.

As understood that the lung segmentation model and/or lung lobe model may be further refined based on external input from a user. The external input is associated with one or more corrections to the outputted validation results. The refinement of the lung segmentation model and/or lung lobe model is iterative and continues until each or both models achieve a pre-determined accuracy threshold in classifying one or more new sets of unsegmented lung images.

For example, the refinement of the lung lobe model may iterate until the single STAGE 1 model or the combined model of STAGE 1 (where the convolutional network may be applied to unsegmented images following initial training) and STAGE 2 (the CNN may be applied to segmented lung images) achieves a pre-determined threshold in accurately classifying one or more new sets of unsegmented lung images. The validation results or results of the model may be compared to one or more annotated lung images of a healthy patient. These stages of the network may be separately configured.

In the example, STAGE 2 follows from STAGE 1 and uses the output from STAGE 1, i.e. the lung segmentation at full resolution to mask the CT image. Explicitly, STAGE 1 receives the original CT image as input and outputs the lung segmentation mask at full resolution. STAGE 2 receives the original CT image, and the lung segmentation mask from STAGE 1. The image which is input to the algorithm for STAGE 2 is the CT image masked by the lung segmentation, i.e. only voxels inside the lung segmentation are used in the training of STAGE 2. STAGE 2 is similar to STAGE 1 except for the change in resolution and the use of the masks from STAGE 1. That is, the resolution becomes finer (if we need to specify, we can say 1 mm^3 vs. 2.8 mm^3 in stage 1) so this allows us to do finer segmentation. The masks from STAGE 1 are used to help guide the segmenter in STAGE 2.

The results from the lung lobe model may be used in the clinical context. One use of the results from the model may be used to determine a dosage regimen for administering antifibrotics drugs to treat lung disease, where lung disease is a type that affects lung airways.

For example, the lung lobe model can be applied to CT scan of the chest that can segment the anatomy of the lobes in a spectrum of conditions from normal lung to severe Interstitial lung diseases (including IPF or related ILDs)

Moreover, when determining a dosage regimen, such determination may be achieving a clinical end-point for administering the drug for treating airway lung diseases such as IPF and related ILDs.

Of the airway model and/or lung lobe model result or output, other applications are to monitor the progression of the lung disease, measure the response to antifibrotics drugs, and the progression of the lung disease in response to such drug treatment. The drug treatment may be drugs for treating cancer or other drugs that may cause or progress lung diseases related to airways. The model output/result may serve as an alternative marker for clinical studies to the standard FVC measures. The marker may be indicative of the drug efficacy or efficacy in relation to the disease progression. The assessment of drug efficacy is in stages, where the assessment is done before and after the drug administration. Alternatively or additionally, the model result may be used to improve clinical trial enrichment, where the result is applied to select a patient with the lung disease at the desired disease progression.

FIG. 2 is a pictorial diagram illustrating an example image 200 of lung images or CT scans from a patient suffering from airway related lung disease such as IPF. The images comprise unsegmented images of the lung 201, 203, and 205 and segmented images of lungs 201a, 203a, and 205a, where the segmented images correspond to the unsegmented ones. The segmentation or annotation associated with the segmentation is highlighted in white. The CT scans of the lung are arranged in perspective from left to right—representing axial plane 201, 201a, coronal plane 203, 203a, and sagittal plane 205, 205a. The segmentation is annotated in the figure. Experts in the field may assist with the segmentation or the annotation process. An enlarged manual segmentation 201b, rendered in 3D, of a sagittal plane, is shown corresponding to the segmented image 201a. The segmented and unsegmented images are used during model training and inference.

FIG. 3 is a schematic diagram illustrating an example of the airway model (similarly with respect to the lung lobe model), where each model is a 3D multistage convolutional network 300. The stages of the network 300 may be distinct from one another, with each stage comprising at least one network layer, filters, and/or kernels. The network layers include a combination of convolutional layers, pooling layers, and fully-connected layers. The final layer of the network is configured to perform classification or regression tasks by applying one or more additional hidden layers that are fully connected to the output layer. The activation function may be a RELU or other suitable functions. The network may also deploy shortcut connections such that gradients flow through the shortcut connection to the earlier layers mitigating the vanishing gradient problem.

An exemplary multistage convolutional network 300 may include but is not limited to: Stage 1: 2.8 mm^3 aquamarine-meerkat; Stage 2: 1.4 mm^3, terrestrial-donkey; and Stage 3: 0.7 mm^3, rich-ferret. These stages of the network may be separately configured.

Starting from a full-size CT scan or image, the network performs resampling of the image 301 at 2.8 mm^3 303, corresponding to Stage 1. A 2.8 mm^3 probability map 305, through convolution, another probability map resampled to 1.4 mm^3 may be derived, forming the basis for the subsequent stage. At stage 2, the image is resampled at 1.4 mm^3 311. Together with the probability map resampled to 1.4 mm^3 307 from stage 1 as an additional colour channel to generate another 1.4 mm^3 probability map 313 resampled to 0.7 mm^3 415. Iteratively and in a similar manner, stage 3 proceeds with generating a using image resampled to 0.7 mm^3 321 with resampled probability map 315 from the previous stage as a colour channel, a 0.7 mm^3 segmentation mask 323 to which may derive a full resolution segmentation mask 325 from the original CT scan/image 301. In this manner, autonomous segmentation is achieved using the airway model.

Figure 4A:
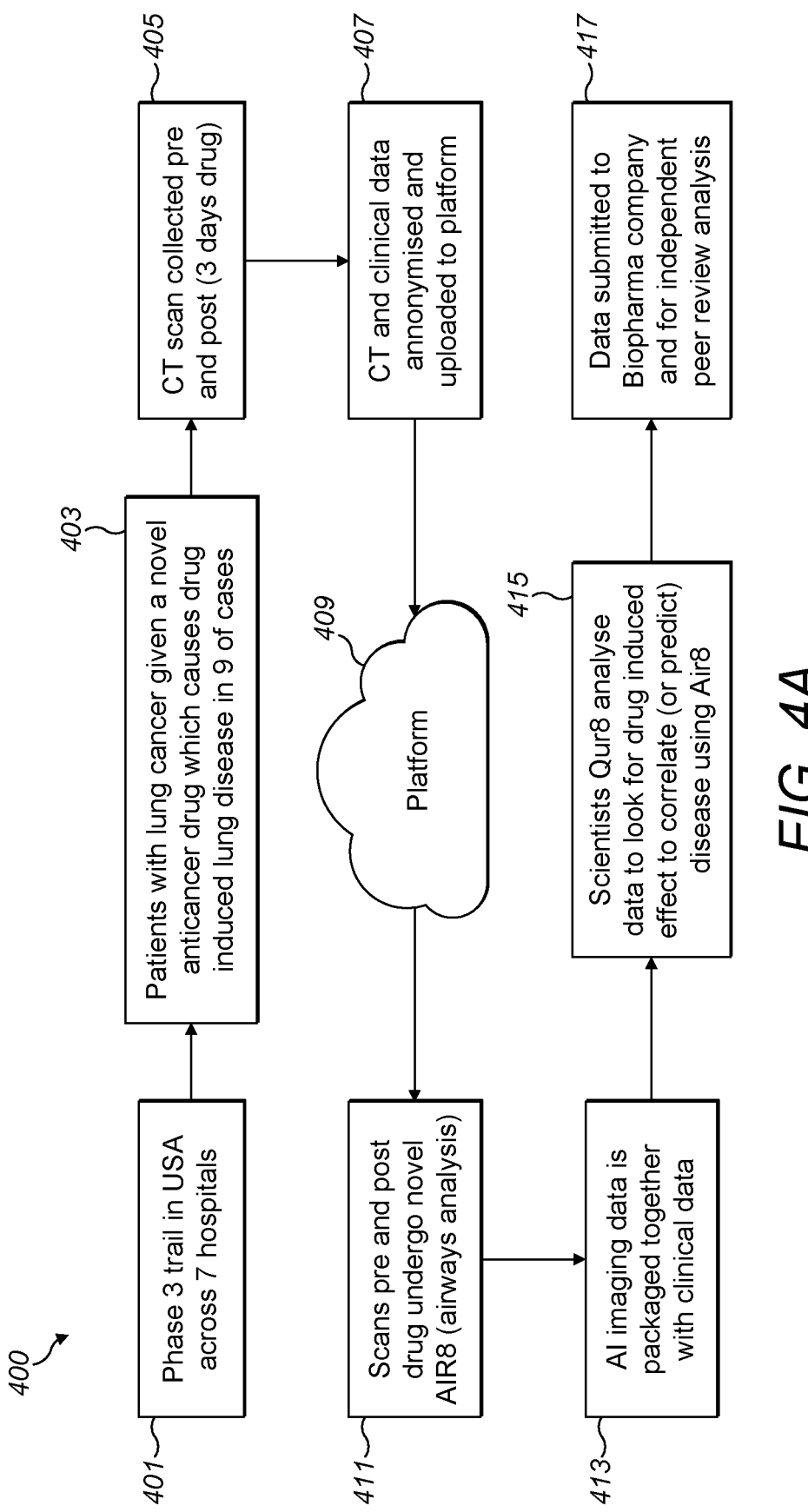
FIG. 4A is a system diagram illustrating an example of an airway model used in the context of the drug discovery according to the invention.

FIG. 4A is a system diagram, illustrating a workflow 400 example of a trained and/or validated airway model according to embodiments associated with FIG. 3 or alternative embodiments of the airway model described herein. The airway model is used in the context of drug discovery and clinical trials, and screening. In the system, the airway model may be used to support or facilitate clinical trials. The system may comprise one or more data storage and at least one processor. The processor may be configured to receive CT scans of a patient with lung disease. The CT scans may be collected from at least two time points. At least one time point is collected before the patient has been administered a drug. One or more time points are collected after the patient has been administered the drug. The system generates a data set associated with the progression of the lung disease from the CT scans by applying a trained airway model and analysing the data set in response to the time point of drug administration. The system determines a drug-induced effect based on the analysis and transmits the determination in support of the clinical study for a particular therapy of a drug candidate.

As part of the workflow 400 of the system diagram, a phase 3 trial 401 may be in process or starting across 7 hospitals. In the trial, the patients with lung disease are given a novel anticancer drug 403, which causes drug-induced lung disease (9% of the case). CT scans together with other clinical data are collected 405 from patients' pre and post drug administration (3 days of the drug dosing). The scans and data are anonymized 407 and updated onto a secured platform 409. Platform 409 may be located on one or more remote servers utilising cloud computing.

From platform 409, the CT scan/images may be retrieved and segmented. The trained and validated airway model (designated as AIR8) may perform analysis based on the CT images. In accordance, the analysis (outputting AI image data) is packaged 411 with the clinical data. Further validation and analysis may be done 415 to the AI image data to look for drug-induced effects to correlate (predict) disease progression using AIR8. The final prediction or results may be submitted for peer review 417.

Figure 5A:
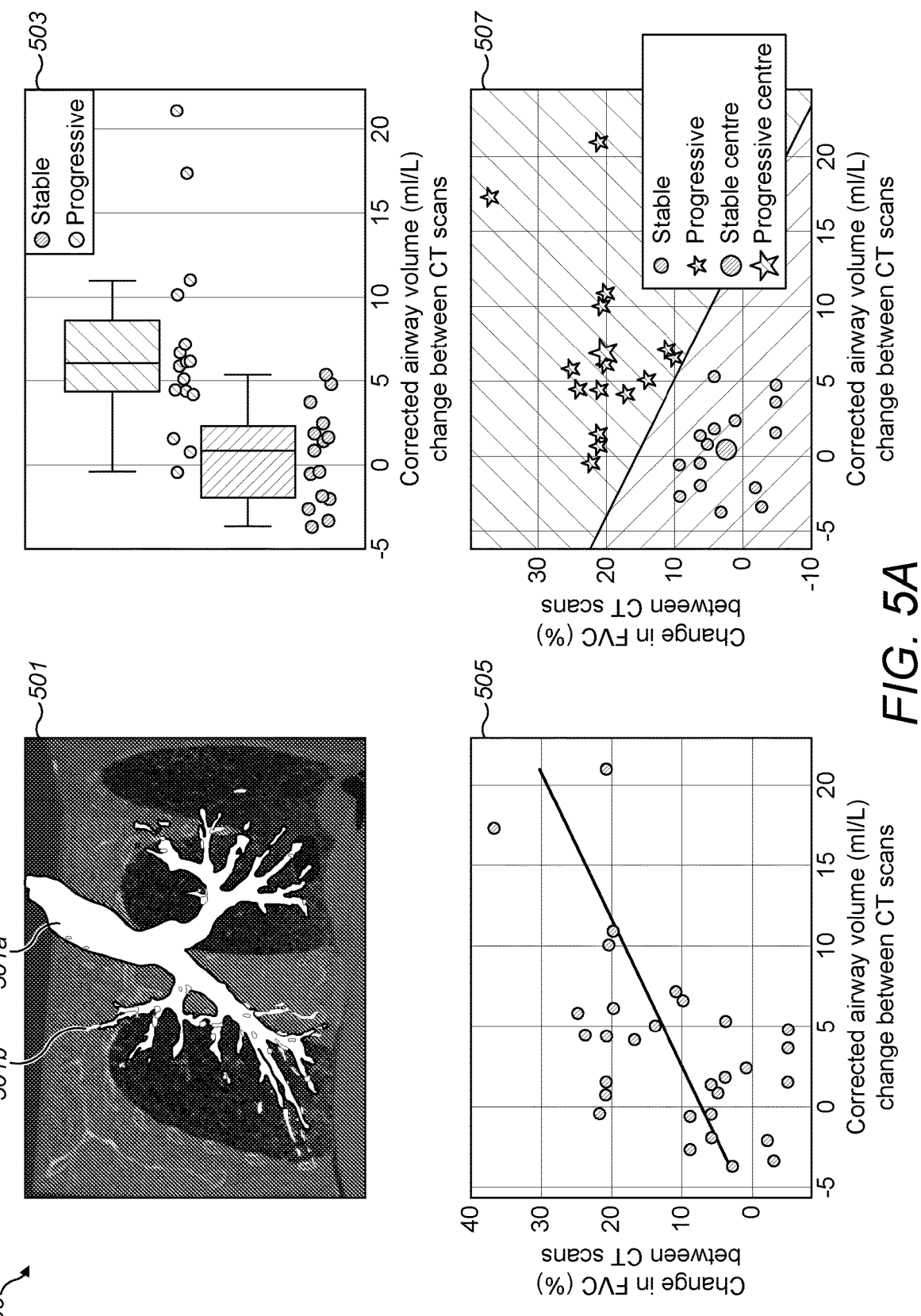
FIG. 5A is a pictorial diagram and charts illustrating an example of an airway model and statistical correlation in respect of the model according to the invention.
Figure 5B:
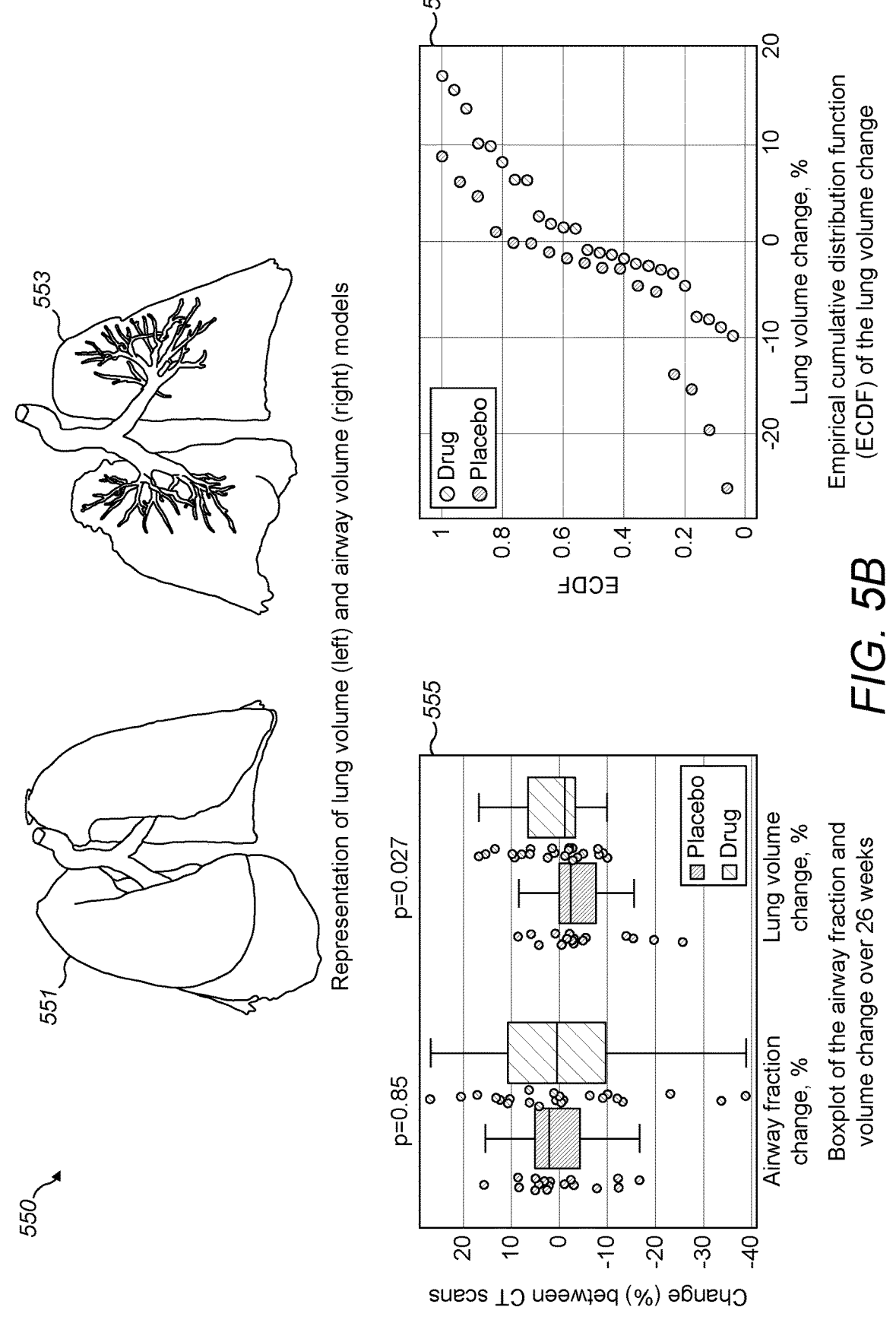
FIG. 5B is a pictorial diagram and charts illustrating an example of an lung lobe model and statistical correlation in respect of the model according to the invention.

FIG. 4B is a diagram illustrating a workflow or system 450 example of a trained and/or validated lung lobe model (designated as LUNG8) according to embodiments associated with FIGS. 1B and 5B or alternative embodiments of the lung lobe model described herein. The system is used in the context of drug discovery and clinical trials, and screening. The system comprises one or more data storage and at least one processor configured to receive computed tomography (CT) scans of a patient with lung disease. The CT scans are collected from at least two time points, at least one time point collected before the patient has been administered a drug, and one or more time points after the patient has been administered the drug. The processor is configured to generate a data set associated with the progression of the lung disease from the CT scans, applying a trained lung lobe model and analysing the data set in response to the time point of drug administration. Based on the analysis, a drug-induced effect is determined as output and transmitted externally in support of the clinical study.

From the workflow, it is understood in relation to FIG. 1B that the workflow 450 progresses iteratively. Double-blinded placebo-controlled studies are performed across multiple sites at 451. The results of which collected and processed by the system. Specifically, at 453, patients with IPF are given a drug with anti-inflammatory activity for treatment in relation to the performed studies. At 455, the CT scans before and after commencement of treatment are at least 26 weeks apart, and at 457, the CT scans and associated clinical data (anonymised) are uploaded onto the system or platform 459 and consequently processed. The system is configured to analyze the CT scans using the lung lobe model at 461. During the analysis, at 463, the processed data may be aggregated with clinical data received. Based on the analysis, a drug-induced effect is determined. At 465, the output may be qualified checked by scientists. A determination is made with respect to whether lung volume changes demonstrates/predict response to treatment compared to standards. At 467, the determination is transmitted externally to Biopharma for peer review and in support of the clinical study.

In respect of workflow in FIGS. 4A and 4B, the trained and/or validated airway model and lung lobe model may be used in a method, system, or as an apparatus for conducting pharmaceutical drug testing or screening to ascertain a response of a candidate drug. The response may be a level of efficacy or toxicity. The candidate drug may be administered to patients affected by or suffering from lung disease. The method, system, or apparatus measures the reaction of the patient to the administration of the candidate drug utilizing a trained model. The measured reaction may be a patient to whom the candidate drug has already been administered, thus utilizing a trained model. The trained model may be configured to receive a first set of unsegmented images from the patient before administration of the candidate drug and a second set of unsegmented images after the administration of the candidate drug. The model determines a baseline of disease progression according to a first set of unsegmented images and the response of disease progression according to a second set of unsegmented images. The model measures the reaction from the patient based on the baseline and the response.

FIG. 5A is a pictorial diagram and charts illustrating an example study 500 of the airway model and statistical correlation in respect of the model. A trained and/or validated airway model is used in the study. Five expert radiologists are employed to segment or annotate airways in 101 IPF patients on CT imaging. Applying a multistage convolutional neural network as its base model and using the segmented CT scans from the experts as the training set, the airway model performs further segmentation from full CT volume. This may be done in an end-to-end manner with the segmentation results continuously refined or iteratively retained until achieving a desirable accuracy. Once fully trained, the airway model is applied to 31 new IPF patients, each with 2 CT scans and contemporaneous pulmonary function testing. The exemplary result of the airway model is shown as graphical representation 501 in the figure. In the graphical representation 501, visualisation of the airway segmentation results is highlighted in white. The main portion of the segmentation 501a shows manual radiologist delineation or annotation, and 501b shows the additional result (or segmentation correction) from the airway model.

In addition to the graphical representation 501 of the airway model, the figure includes three charts showing the correlation between FVC and airway size changes based on CT scans.

In chart 503, the patients are divided into two groups: stable (<10% FVC change between scans and specialist MDT review confirming stability on CT, n=15) and progressive (>10% FVC change, MDT review confirming progressive, n=16). Application of our model showed a difference in median airway size change between groups, with a larger increase in the progressive group (32.4% vs 8.6% p=0.001, 6 ml/L vs 0.8 ml/L corrected lung volume p=0.0003). The chart shows airway change in ml/L (corrected for lung volume) between CT scans in stable vs progressive groups.

Chart 505 shows corrected airway change against change in FVC—in particular, showing the lung volume declined in both groups, greater in the progressive group (−15.4% vs −6.7%). It can be seen that the change in airway size and FVC are correlated.

Chart 507 is the unsupervised classification results based on airway volume change in addition to the change in FVC. A similar grouping as Chart 503 is applied and shown in the chart. Accepting limitations in preselecting FVC groups (including groups for stable centre and progressive centre), the application of unsupervised (K-Means) machine learning attempts to classify patients into two distinct clusters when changing airway volume to FVC. It can be understood that the traction bronchiectasis is known to correlate with IPF progression but is time-consuming and requires expert radiologists. The study therefore correlates well with radiological progression. Change in airway size may be used as surrogate marker for clinical progression.

FIG. 5B is a pictorial diagram and charts illustrating an example study 550 of the lung lobe model and statistical correlation in respect of the model. Trained and/or validated lung/lobe models are used in the study. Five expert radiologists are employed to segment or annotate lungs and lobes of IPF patients on CT imaging. Applying a multistage convolutional neural network as its base model and using the CT scans from the experts as the training set, the lung lobe model performs further segmentation from full CT volume. This may be done in an end-to-end manner with the segmentation results continuously refined or iteratively retained until achieving a desirable accuracy.

The exemplary result of the lung lobe model is shown as graphical representations 551 and 553 in the figure. In the graphical representation, visualisation of the airway segmentation results is highlighted in white. The main portion of the segmentation 551 shows manual radiologist delineation or annotation, and 553 shows the additional result (or segmentation correction) from the airway model in comparison.

Chart 555 shows the results of a double-blind placebo controlled study of a new IPF in drug in 68 patients. Computed CT volumes identified a significant difference in lung volume change over 26 weeks between subjected administered IPF drug (+1.51%) vs those administered placebo (−4.48%) p=0.027. On this specific study no statistically significant difference is seen in airway fraction change between the two groups likely related to the small number of patients.

Chart 557 reports the empirical cumulative distribution function (ECDF) of the lung volume change. This demonstrates that lung volume changes are able to differentiate the placebo and the drug groups.

Figure 6:
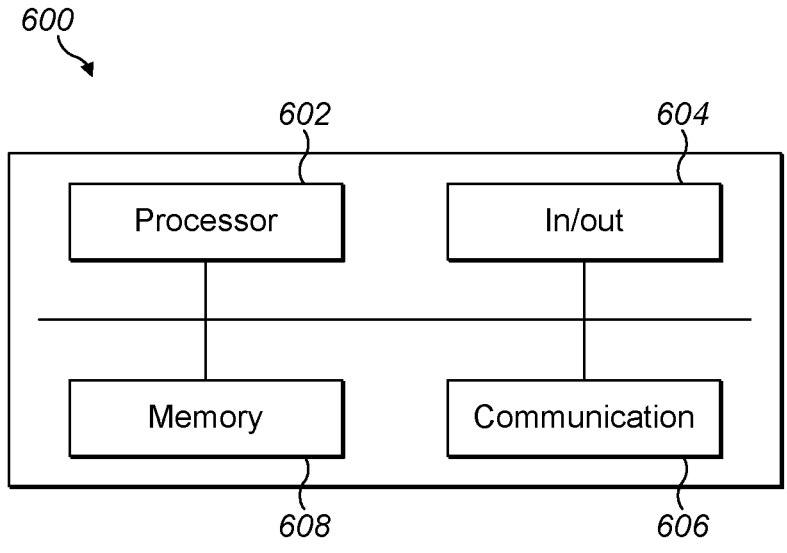
FIG. 6 is a block diagram of a computing device suitable for implementing embodiments of the invention.

FIG. 6 is a block diagram illustrating an example computing apparatus/system 600 that may be used to implement one or more aspects of the system(s), apparatus, method(s), and/or process(es) combinations thereof, modifications thereof, and/or as described with reference to FIGS. 1 to 5 and/or as described herein. Computing apparatus/system 600 includes one or more processor unit(s) 602, an input/output unit 604, communications unit/interface 606, a memory unit 608 in which the one or more processor unit(s) 602 are connected to the input/output unit 604, communications unit/interface 606, and the memory unit 608. In some embodiments, the computing apparatus/system 600 may be a server, or one or more servers networked together. In some embodiments, the computing apparatus/system 600 may be a computer or supercomputer/processing facility or hardware/software suitable for processing or performing the one or more aspects of the system(s), apparatus, method(s), and/or process(es) combinations thereof, modifications thereof, and/or as described with reference to FIGS. 1 to 5 and/or as described herein. The communications interface 606 may connect the computing apparatus/system 600, via a communication network, with one or more services, devices, the server system(s), cloud-based platforms, systems for implementing subject-matter databases and/or knowledge graphs for implementing the invention as described herein. The memory unit 608 may store one or more program instructions, code or components such as, by way of example only but not limited to, an operating system and/or code/component(s) associated with the process(es)/method(s) as described with reference to FIGS. 1 to 5, additional data, applications, application firmware/software and/or further program instructions, code and/or components associated with implementing the functionality and/or one or more function(s) or functionality associated with one or more of the method(s) and/or process(es) of the device, service and/or server(s) hosting the process(es)/method(s)/system(s), apparatus, mechanisms and/or system(s)/platforms/architectures for implementing the invention as described herein, combinations thereof, modifications thereof, and/or as described with reference to at least one of the FIGS. 1 to 5.

One aspect of the present disclosure provides a computer-implemented method of preparing a lung lobe model for assessing progression of a lung disease, the method comprising: receiving a first set of segmented images of lungs from patients with different severities of the lung disease, wherein the images in the first set are segmented using a trained lung segmentation model; training the lung lobe model using the first set of segmented images based on segmentation of the images in the first set and lung morphology associated with the segmentation, wherein the lung morphology comprises at least lobes of left and right lungs; applying the trained lung lobe model to a set of unsegmented images of lungs from different patients to generate a second set of segmented images, wherein the set of unsegmented images corresponds to the first set of segmented images; updating the trained lung lobe model with the second set of segmented images; and providing the updated lung lobe model configured to output at least one results associated with the lung disease progression of a patient.

Another aspect of the present disclosure provides a computer-implemented method or method of preparing an airway model for assessing progression of a lung disease, the method comprising: receiving a first set of segmented images of lungs from different patients with the lung disease associated with airways, wherein the first set of images is segmented manually based on a generational level of airway; training the model using the first set of segmented images, wherein the model is configured to segment the airways based on airway morphological parameters; applying the model to a set of unsegmented images to generate a second set of segmented images, wherein the set of unsegmented images corresponds to the first set of segmented images; updating the model with the second set of segmented segmentation; and outputting, from the model, at least one result associated with the lung disease progression of a patient.

Another aspect of the present disclosure provides a method for conducting pharmaceutical drug testing to ascertain a response of a candidate drug comprising: administering the candidate drug to a patient affected by lung disease; and measuring a reaction of the patient to the administration of the candidate drug utilizing a trained airway model and/or a trained lung lobe model, wherein each model is configured to: receive a first set of unsegmented images from the patient before administration of the candidate drug and a second set of unsegmented images after the administration of the candidate drug; determine a baseline of disease progression according to a first set of unsegmented images; determine the response of disease progression according to a second set of unsegmented images; and measure the reaction from the patient based on the baseline and the response.

Another aspect of the present disclosure provides a method for conducting pharmaceutical drug screening to ascertain a response of a candidate drug for lung disease, the method comprising: measuring a reaction of a patient suffering from lung disease to whom the candidate drug has been administered utilizing a trained airway model and/or a trained lung lobe model, wherein each model is configured to: receive a first set of unsegmented images from the patient before administration of the candidate drug and a second set of unsegmented images after the administration of the candidate drug; determine a baseline of disease progression according to a first set of unsegmented images; determine the response of disease progression according to a second set of unsegmented images; and measure the reaction from the patient based on the baseline and the response.

Another aspect of the present disclosure provides a system for supporting a clinical study, the system comprising: one or more data storages and at least one processor configured to: receive computed tomography (CT) scans of a patient with lung disease, wherein the CT scans are collected from at least two time points, at least one time point collected before the patient has been administered a drug, and one or more time points after the patient has been administered the drug; generate a data set associated with progression of the lung disease from the CT scans applying a trained airway model and/or a trained lung lobe model; analyse the data set in response to the time point of drug administration; determine a drug-induced effect based on the analysis; and transmit the determination in support of the clinical study.

Another aspect of the present disclosure provides an apparatus comprising a processor comprising a processor, a memory and a communication interface, the processor connected to the memory and communication interface, wherein apparatus is adapted or configured to: prepare an airway model for assessing progression of a lung disease, the method comprising: receiving a first set of segmented images of lungs from different patients with the lung disease associated with airways, wherein the first set of images is segmented manually based on a generational level of airway; training the model using the first set of segmented images, wherein the model is configured to segment the airways based on airway morphological parameters; applying the model to a set of unsegmented images to generate a second set of segmented images, wherein the set of unsegmented images corresponds to the first set of segmented images; updating the model with the second set of segmented segmentation; and outputting, from the model, at least one result associated with the lung disease progression of a patient.

Another aspect of the present disclosure provides an apparatus comprising a processor comprising a processor, a memory and a communication interface, the processor connected to the memory and communication interface, wherein apparatus is adapted or configured to: conduct pharmaceutical drug testing or screening to ascertain a response of a candidate drug for lung disease, the method comprising: measuring a reaction of a patient suffering from lung disease to whom the candidate drug has been administered utilizing a trained airway model and/or a trained lung lobe model, wherein each model is configured to: receive a first set of unsegmented images from the patient before administration of the candidate drug and a second set of unsegmented images after the administration of the candidate drug; determine a baseline of disease progression according to a first set of unsegmented images; determine the response of disease progression according to a second set of unsegmented images; and measure the reaction from the patient based on the baseline and the response.

Another aspect of the present disclosure provides a system for supporting a clinical study, the system comprising: one or more data storages and at least one processor configured to: receive computed tomography (CT) scans of a patient with lung disease, wherein the CT scans are collected from at least two time points, at least one time point collected before the patient has been administered a drug, and one or more time points after the patient has been administered the drug; generate a data set associated with progression of the lung disease from the CT scans applying a trained airway model and/or a trained lung lobe model; analyse the data set in response to the time point of drug administration; determine a drug-induced effect based on the analysis; and transmit the determination in support of the clinical study.

It is understood that the following options could be combined, apparent to a skilled person, with any of the above aspects go far as to achieve one or more advantages of the present invention.

As one option, the first set of segmented images comprises segmented lung images masked by segmentation of the lungs derived using the trained lung segmentation model from a set of unsegmented computed tomography (CT) images of lungs. As another option, the trained lung segmentation model is configured to: receive a set of unsegmented computed tomography (CT) images of lungs;

process unsegmented CT images of lungs at one or more resampling dimensions in relation to a probability map; generate the probability map associated with said one or more resampling dimensions; and provide the first set of segmented images from the unsegmented CT images of lungs based on the probability map. As another option, the first set of segmented images is provided at a full image resolution corresponding to an original image resolution of the set of unsegmented CT images of lungs. As another option, furthering comprising: training a lung segmentation model, wherein the lung segmentation model is configured to: receive a set of computed tomography (CT) images of lungs annotated with at least one designated segmentation; process the set of annotated CT images of lungs based on the said at least one designated segmentation at one or more resampling dimensions; generate the probability map associated with said one or more resampling dimensions in relation to said at least one designated segmentation; and provide the trained lung segmentation model comprises the generated probability map. As another option, further comprising: validating the lung lobe model with a new set of unsegmented images; and outputting the validation results from the lung lobe model. As another option, further comprising: comparing the validation results to one or more annotated lung images of a healthy patient and/or a patient suffering from the lung disease to assess disease progression associated with each image from the set of unsegmented lung images. As another option, further comprising: refining the lung segmentation model and/or lung lobe model based on an external input from a user, wherein the external input is associated with one or more corrections to the outputted validation results. As another option, further comprising: iterating the refinement of the lung segmentation model and/or lung lobe model until each or both models achieve a predetermined accuracy threshold in classifying one or more new sets of unsegmented lung images. As another option, further comprising: outputting, from the trained lung lobe model, said at least one result associated with the lung disease progression of the patient based on a new set of unsegmented lung images from the patient. As another option, said at least one result is used to determine a dosage regimen for administering a drug to treat the lung disease. As another option, the lung disease is a type that affects lung airways. As another option, the lung disease is Idiopathic Pulmonary Fibrosis (IPF) or a related interstitial lung disease (ILD). As another option, said determining the dosage regime comprises achieving a clinical end-point for administering the drug for treating IPF or a related ILD. As another option, the drug is a type of antifibrotic. As another option, said at least one result is used for monitoring the progression of the lung disease in response to drug treatment. As another option, the outputted at least one result is used for improving clinical trial enrichment, wherein said at least one result is applied to select a patient with the lung disease at a desired disease progression. As another option, the lung segmentation model and/or lung lobe model configured to capture the spatial and temporal dependencies in an input image. As another option, the lung segmentation model and/or lung lobe model is a type of convolutional neural network.

As another option, further comprising: validating the model with a new set of unsegmented images; and outputting the validation results from the model. As another option, further comprising: refining the model based on an external input from a user, wherein the external input is associated with one or more corrections to the outputted validation results. As another option, further comprising: iterating the refinement of the model until the model achieves a predetermined accuracy threshold in classifying one or more new sets of unsegmented lung images. As another option, further comprising: comparing the validation results to one or more annotated lung images of a healthy patient and/or a patient suffering from the lung disease to assess disease progression associated with each image from the set of unsegmented lung images. As another option, wherein the airways comprise at least trachea, main bronchi, lobar bronchi, segmental and subsegmental bronchi. As another option, wherein said segmented and unsegmented images comprise one or more types of computed tomography (CT) images of lungs. As another option, wherein the first set of segmented images, the second set of segmented images, and the set of unsegmented images are generated using or derived from a device with an X-ray source. As another option, wherein said airway morphological parameters comprise airway size, airway diameter, airway volume, pattern of airway branching, and degree of airway branching. As another option, wherein the airway diameter is associated with a tissue condition in relation to a stage of disease progression, wherein the tissue condition comprises healthy issue and traction bronchiectasis. As another option, wherein said at least one result is used for determining a dosage regimen for administering a drug to treat the lung disease. As another option, wherein the lung disease is a type that affects lung airways. As another option, wherein the lung disease is IPF or ILD. As another option, wherein said determining the dosage regime comprises achieving a clinical end-point for administering the drug for treating IPF or ILD. As another option, wherein said at least one result is used for monitoring the progression of the lung disease in response to drug treatment. As another option, wherein the drug is a type of antifibrotic agent, drug, or treatment, therapy. As another option, wherein the outputted at least one result is used for improving clinical trial enrichment, wherein said at least one result is applied to select a patient with the lung disease at a desired disease progression. As another option, wherein the model configured to capture the spatial and temporal dependencies in an input image. As another option, wherein the model is a type of convolutional neural network.

In the embodiments, examples, and aspects of the invention as described above such as process(es), method(s), system(s) and/or apparatus may be implemented on and/or comprise one or more cloud platforms, one or more server(s) or computing system(s) or device(s). A server may comprise a single server or network of servers; the cloud platform may include a plurality of servers or network of servers. In some examples the functionality of the server and/or cloud platform may be provided by a network of servers distributed across a geographical area, such as a worldwide distributed network of servers, and a user may be connected to an appropriate one of the network of servers based upon a user location and the like.

The above description discusses embodiments of the invention with reference to a single user for clarity. It will be understood that in practice, the system may be shared by a plurality of users, and possibly by a very large number of users simultaneously.

The embodiments described above may be configured to be semi-automatic and/or are configured to be fully automatic. In some examples a user or operator of the querying system(s)/process(es)/method(s) may manually instruct some steps of the process(es)/method(es) to be carried out.

The described embodiments of the invention a system, process(es), method(s) and/or apparatus according to the invention and/or as herein described may be implemented as any form of a computing and/or electronic device. Such a device may comprise one or more processors which may be microprocessors, controllers or any other suitable type of processors for processing computer executable instructions to control the operation of the device in order to gather and record routing information. In some examples, for example where a system on a chip architecture is used, the processors may include one or more fixed function blocks (also referred to as accelerators) which implement a part of the process/method in hardware (rather than software or firmware). Platform software comprising an operating system or any other suitable platform software may be provided at the computing-based device to enable application software to be executed on the device.

Various functions described herein can be implemented in hardware, software, or any combination thereof. If implemented in software, the functions can be stored on or transmitted over as one or more instructions or code on a computer-readable medium or non-transitory computer-readable medium. Computer-readable media may include, for example, computer-readable storage media. Computer-readable storage media may include volatile or non-volatile, removable or non-removable media implemented in any method or technology for storage of information such as computer-readable instructions, data structures, program modules or other data. A computer-readable storage media can be any available storage media that may be accessed by a computer. By way of example, and not limitation, such computer-readable storage media may comprise RAM, ROM, EEPROM, flash memory or other memory devices, CD-ROM or other optical disc storage, magnetic disc storage or other magnetic storage devices, or any other medium that can be used to carry or store desired program code in the form of instructions or data structures and that can be accessed by a computer. Disc and disk, as used herein, include compact disc (CD), laser disc, optical disc, digital versatile disc (DVD), floppy disk, and blu-ray disc (BD). Further, a propagated signal is not included within the scope of computer-readable storage media. Computer-readable media also includes communication media including any medium that facilitates transfer of a computer program from one place to another. A connection or coupling, for instance, can be a communication medium. For example, if the software is transmitted from a website, server, or other remote source using a coaxial cable, fiber optic cable, twisted pair, DSL, or wireless technologies such as infrared, radio, and microwave are included in the definition of communication medium. Combinations of the above should also be included within the scope of computer-readable media.

Alternatively, or in addition, the functionality described herein can be performed, at least in part, by one or more hardware logic components. For example, and without limitation, hardware logic components that can be used may include Field-programmable Gate Arrays (FPGAs), Program-specific Integrated Circuits (ASICs), Program-specific Standard Products (ASSPs), System-on-a-chip systems (SOCs). Complex Programmable Logic Devices (CPLDs), etc.

Although illustrated as a single system, it is to be understood that the computing device may be a distributed system. Thus, for instance, several devices may be in communication by way of a network connection and may collectively perform tasks described as being performed by the computing device.

Although illustrated as a local device it will be appreciated that the computing device may be located remotely and accessed via a network or other communication link (for example using a communication interface).

The term 'computer' is used herein to refer to any device with processing capability such that it can execute instructions. Those skilled in the art will realise that such processing capabilities are incorporated into many different devices and therefore the term 'computer' includes PCs, servers, IoT devices, mobile telephones, personal digital assistants and many other devices.

Those skilled in the art will realise that storage devices utilised to store program instructions can be distributed across a network. For example, a remote computer may store an example of the process described as software. A local or terminal computer may access the remote computer and download a part or all of the software to run the program. Alternatively, the local computer may download pieces of the software as needed, or execute some software instructions at the local terminal and some at the remote computer (or computer network). Those skilled in the art will also realise that by utilising conventional techniques known to those skilled in the art that all, or a portion of the software instructions may be carried out by a dedicated circuit, such as a DSP, programmable logic array, or the like.

It will be understood that the benefits and advantages described above may relate to one embodiment or may relate to several embodiments. The embodiments are not limited to those that solve any or all of the stated problems or those that have any or all of the stated benefits and advantages. Variants to the described embodiments should be included into the scope of the invention.

Any reference to 'an' item refers to one or more of those items. The term 'comprising' is used herein to mean including the method steps or elements identified, but that such steps or elements do not comprise an exclusive list and a method or apparatus may contain additional steps or elements.

As used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary", "example" or "embodiment" is intended to mean "serving as an illustration or example of something". Further, to the extent that the term "includes" is used in either the detailed description or the claims, such term is intended to be inclusive in a manner similar to the term "comprising" as "comprising" is interpreted when employed as a transitional word in a claim.

The figures illustrate exemplary methods. While the methods are shown and described as being a series of acts that are performed in a particular sequence, it is to be understood and appreciated that the methods are not limited by the order of the sequence. For example, some acts can occur in a different order than what is described herein. In addition, an act can occur concurrently with another act. Further, in some instances, not all acts may be required to implement a method described herein.

Moreover, the acts described herein may comprise computer-executable instructions that can be implemented by one or more processors and/or stored on a computer-readable medium or media. The computer-executable instructions can include routines, sub-routines, programs, threads of execution, and/or the like. Still further, results of acts of the methods can be stored in a computer-readable medium, displayed on a display device, and/or the like.

The order of the steps of the methods described herein is exemplary, but the steps may be carried out in any suitable order, or simultaneously where appropriate. Additionally, steps may be added or substituted in, or individual steps may be deleted from any of the methods without departing from the scope of the subject matter described herein. Aspects of any of the examples described above may be combined with aspects of any of the other examples described to form further examples without losing the effect sought.

It will be understood that the above description of a preferred embodiment is given by way of example only and that various modifications may be made by those skilled in the art.

What has been described above includes examples of one or more embodiments. It is, of course, not possible to describe every conceivable modification and alteration of the above devices or methods for purposes of describing the aforementioned aspects, but one of ordinary skill in the art can recognize that many further modifications and permutations of various aspects are possible. Accordingly, the described aspects are intended to embrace all such alterations, modifications, and variations that fall within the scope of the appended claims.

The invention claimed is:

1. A computer-implemented method of preparing a lung lobe model for assessing progression of a lung disease, the method comprising:
   receiving a first set of segmented images of lungs from patients with different severities of the lung disease, wherein the images in the first set are segmented using a trained lung segmentation model;
   training the lung lobe model using the first set of segmented images based on segmentation of the images in the first set and lung morphology associated with the segmentation, wherein the lung morphology comprises at least lobes of left and right lungs;
   applying the trained lung lobe model to a set of unsegmented images of lungs from different patients to generate a second set of segmented images, wherein the set of unsegmented images corresponds to the first set of segmented images;
   updating the trained lung lobe model with the second set of segmented images; and
   providing the updated lung lobe model configured to output at least one results associated with the lung disease progression of a patient.

2. The method of claim 1, wherein the first set of segmented images comprises segmented lung images masked by segmentation of the lungs derived using the trained lung segmentation model from a set of unsegmented computed tomography (CT) images of lungs.

3. The method of claim 1, wherein the trained lung segmentation model is configured to:
   receive a set of unsegmented computed tomography (CT) images of lungs;
   process unsegmented CT images of lungs at one or more resampling dimensions in relation to a probability map;
   generate the probability map associated with said one or more resampling dimensions; and
   provide the first set of segmented images from the unsegmented CT images of lungs based on the probability map.

4. The method of claim 3, wherein the first set of segmented images is provided at a full image resolution corresponding to an original image resolution of the set of unsegmented CT images of lungs.

5. The method of claim 1, furthering comprising: training a lung segmentation model, wherein the lung segmentation model is configured to:

receive a set of computed tomography (CT) images of lungs annotated with at least one designated segmentation;

process the set of annotated CT images of lungs based on the said at least one designated segmentation at one or more resampling dimensions;

generate the probability map associated with said one or more resampling dimensions in relation to said at least one designated segmentation; and provide the trained lung segmentation model comprises the generated probability map.

6. The method of claim 1, further comprising: validating the lung lobe model with a new set of unsegmented images; and outputting the validation results from the lung lobe model.

7. The method of claim 6, further comprising: comparing the validation results to one or more annotated lung images of a healthy patient and/or a patient suffering from the lung disease to assess disease progression associated with each image from the set of unsegmented lung images.

8. The method of claim 6, further comprising: refining the lung segmentation model and/or lung lobe model based on an external input from a user, wherein the external input is associated with one or more corrections to the outputted validation results.

9. The method of claim 8, further comprising: iterating the refinement of the lung segmentation model and/or lung lobe model until each or both models achieve a pre-determined accuracy threshold in classifying one or more new sets of unsegmented lung images.

10. The method of claim 1, further comprising: outputting, from the trained lung lobe model, said at least one result associated with the lung disease progression of the patient based on a new set of unsegmented lung images from the patient.

11. The method of claim 10, wherein said at least one result is used to determine a dosage regimen for administering a drug to treat the lung disease.

12. The method of claim 1, wherein the lung disease is a type that affects lung airways.

13. The method of claim 1, wherein the lung disease is Idiopathic Pulmonary Fibrosis (IPF) or a related interstitial lung disease (ILD).

14. The method of claim 11, wherein said determining the dosage regime comprises achieving a clinical end-point for administering the drug for treating IPF or a related ILD.

15. The method of claim 11, wherein the drug is a type of antifibrotic.

16. The method of claim 1, wherein said at least one result is used for monitoring the progression of the lung disease in response to drug treatment.

17. The method of claim 1, wherein the outputted at least one result is used for improving clinical trial enrichment, wherein said at least one result is applied to select a patient with the lung disease at a desired disease progression.

18. The method of claim 1, wherein the lung segmentation model and/or lung lobe model is configured to capture the spatial and temporal dependencies in an input image.

19. The method of claim 1, wherein the lung segmentation model and/or lung lobe model is a type of convolutional neural network.

20. A computer-implemented method of preparing an airway model for assessing progression of a lung disease, the method comprising:

28 receiving a first set of segmented images of lungs from different patients with the lung disease associated with airways, wherein the first set of images is segmented manually based on a generational level of airway;

training the model using the first set of segmented images, wherein the model is configured to segment the airways based on airway morphological parameters;

applying the model to a set of unsegmented images to generate a second set of segmented images, wherein the set of unsegmented images corresponds to the first set of segmented images;

updating the model with the second set of segmented segmentation; and outputting, from the model, at least one result associated with the lung disease progression of a patient.

21. The method of claim 20, further comprising: validating the model with a new set of unsegmented images; and outputting the validation results from the model.

22. The method of claim 21, further comprising: refining the model based on an external input from a user, wherein the external input is associated with one or more corrections to the outputted validation results.

23. The method of claim 22, further comprising: iterating the refinement of the model until the model achieves a pre-determined accuracy threshold in classifying one or more new sets of unsegmented lung images.

24. The method of claim 21, further comprising: comparing the validation results to one or more annotated lung images of a healthy patient and/or a patient suffering from the lung disease to assess disease progression associated with each image from the set of unsegmented lung images.

25. The method of claim 20, wherein the airways comprise at least trachea, main bronchi, lobar bronchi, segmental and subsegmental bronchi.

26. The method of claim 20, wherein said segmented and unsegmented images comprise one or more types of computed tomography (CT) images of lungs.

27. The method of claim 20, wherein the first set of segmented images, the second set of segmented images, and the set of unsegmented images are generated using or derived from a device with an X-ray source.

28. The method of claim 20, wherein said airway morphological parameters comprise airway size, airway diameter, airway volume, pattern of airway branching, and degree of airway branching.

29. The method of claim 28, wherein the airway diameter is associated with a tissue condition in relation to a stage of disease progression, wherein the tissue condition comprises healthy issue and traction bronchiectasis.

30. The method of claim 20, wherein said at least one result is used for determining a dosage regimen for administering a drug to treat the lung disease.

31. The method of claim 20, wherein the lung disease is a type that affects lung airways.

32. The method of claim 20, wherein the lung disease is IPF or a related ILD.

33. The method of claim 30, wherein said determining the dosage regime comprises achieving a clinical end-point for administering the drug for treating IPF or a related ILD.

34. The method of claim 20, wherein said at least one result is used for monitoring the progression of the lung disease in response to drug treatment.

35. The method of claim 30, wherein the drug is a type of antifibrotic.

36. The method of claim 20, wherein the outputted at least one result is used for improving clinical trial enrichment, wherein said at least one result is applied to select a patient with the lung disease at a desired disease progression.

37. The method of claim 20, wherein the model is configured to capture the spatial and temporal dependencies in an input image.

38. The method of claim 20, wherein the model is a type of convolutional neural network.

39. The method of claim 20, wherein:

the first set of segmented images are from different patients with a lung disease that affects lung airways, including Idiopathic Pulmonary Fibrosis, IPF, or a related Interstitial Lung Disease, ILD;

the airway model comprises a multistage convolutional neural network configured to capture at least spatial dependencies in an input image;

the airway model is configured to segment, based on the captured spatial dependencies, the airways based on airway morphological parameters comprising airway size, airway diameter, airway volume, pattern of airway branching, and degree of airway branching;

the second set of segmented images are comparable to the first set of segmented images; and said outputting comprises applying the updated airway model to one or more new unsegmented lung images from a patient obtained at different time points, to output at least one result associated with the IPF or ILD progression of the patient.

40. The method of claim 39, wherein the airway model is configured to receive a full-size three-dimensional CT image, wherein the full-size three-dimensional CT image is resampled to a plurality of different resolutions, wherein each of the plurality of different resolutions is input to a different stage of the multistage convolutional neural network, and wherein a probability map output from a previous stage at a first resolution is resampled and provided as input along with the resampled three-dimensional CT image at a second resolution, the first resolution being lower than the second resolution.

41. The method of claim 40, wherein the stages of the multistage convolutional neural network correspond to airway diameters in the airway morphological parameters.

42. The method of claim 1, wherein:

the first set of segmented images are from different patients with a lung disease including Idiopathic Pulmonary Fibrosis, IPF, or a related Interstitial Lung Disease, ILD;

the lung lobe model comprises a multistage convolutional neural network configured to capture at least spatial dependencies in an input image;

the lung lobe model is configured to segment based on the captured spatial dependencies;

the second set of segmented images are comparable to the first set of segmented images; and said outputting comprises applying the updated lung lobe model to one or more new unsegmented lung images from a patient obtained at different time points, to output at least one result associated with the IPF or ILD progression of the patient.

43. The method of claim 42, wherein the lung lobe model is configured to receive a full-size three-dimensional CT image, wherein the full-size three-dimensional CT image is resampled to a plurality of different resolutions, wherein each of the plurality of different resolutions is input to a different stage of the multistage convolutional neural network, and wherein a probability map output from a previous stage at a first resolution is resampled and provided as input along with the resampled three-dimensional CT image at a second resolution, the first resolution being lower than the second resolution.

\* \* \* \* \*